(12) United States Patent
Huang et al.

(10) Patent No.: US 11,090,391 B2
(45) Date of Patent: Aug. 17, 2021

(54) PROTEIN NANOCAGES WITH ENHANCED MUCUS PENETRATION FOR TARGETED TISSUE AND INTRACELLULAR DELIVERY

(71) Applicant: The Johns Hopkins University, Baltimore, MD (US)

(72) Inventors: Xinglu Huang, Bethesda, MD (US); Jung Soo Suk, Baltimore, MD (US); Justin Hanes, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 16/333,501

(22) PCT Filed: Sep. 18, 2017

(86) PCT No.: PCT/US2017/052079
§ 371 (c)(1),
(2) Date: Mar. 14, 2019

(87) PCT Pub. No.: WO2018/053434
PCT Pub. Date: Mar. 22, 2018

(65) Prior Publication Data
US 2019/0255189 A1    Aug. 22, 2019

Related U.S. Application Data

(60) Provisional application No. 62/395,852, filed on Sep. 16, 2016.

(51) Int. Cl.
| A61K 38/00 | (2006.01) |
| A61K 47/69 | (2017.01) |
| A61K 47/64 | (2017.01) |
| A61K 47/60 | (2017.01) |
| A61K 9/00  | (2006.01) |
| A61K 9/50  | (2006.01) |
| A61K 31/704 | (2006.01) |

(52) U.S. Cl.
CPC ........ *A61K 47/6931* (2017.08); *A61K 9/0019* (2013.01); *A61K 9/5052* (2013.01); *A61K 31/704* (2013.01); *A61K 47/60* (2017.08); *A61K 47/64* (2017.08); *A61K 47/6929* (2017.08)

(58) Field of Classification Search
None
See application file for complete search history.

(56) References Cited

U.S. PATENT DOCUMENTS

| 5,034,506 A | 7/1991 | Summerton |
| 5,571,711 A | 11/1996 | Van Der Bruggen |
| 5,683,886 A | 11/1997 | Van Der Bruggen |
| 6,673,545 B2 | 1/2004 | Faris |
| 6,677,157 B1 | 1/2004 | Cohen |
| 2006/0110383 A1 | 5/2006 | Honjo |
| 2007/0258889 A1 | 11/2007 | Douglas |
| 2015/0224212 A1 | 8/2015 | Park |

FOREIGN PATENT DOCUMENTS

| GB | 2241703 | 9/1991 |
| WO | 9640039 | 12/1996 |
| WO | 0050900 | 8/2000 |
| WO | 2003099196 | 12/2003 |
| WO | 2004004771 | 1/2004 |
| WO | 2004056875 | 7/2004 |
| WO | 2004072286 | 8/2004 |
| WO | 2006121168 | 2/2006 |
| WO | 2006133396 | 2/2006 |
| WO | 2007005874 | 1/2007 |
| WO | 2008083174 | 1/2008 |
| WO | 2009014708 | 1/2009 |
| WO | 2009073533 | 6/2009 |
| WO | 2016048246 | 3/2016 |

OTHER PUBLICATIONS

Doll et al. Journal of Nanobiotechnology, vol. 13, Article No. 73, 2015.*
Soo Suk et al. Adv Drug Deliv Rev. Apr. 1, 2016; 99(Pt A): 28-51.*
Arora, et al., Nanocarriers Enhance Doxorubicin Uptake in Drug-Resistant Ovarian Cancer Cells Cancer Res, 72:769-78 (2012).
Barua, et al, "Challenges associated with Penetration of Nanoparticles across Cell and Tissue Barriers: A Review of Current Status and Future Prospects", Nano Today, 9:223-43 (2014).
Cabral, et al, "Accumulation of sub-100 nm polymeric micelles in poorly permeable tumours depends on size", Nat Nanotechnol, 6:815-23 (2011).
Chauhan, et al., "Normalization of tumour blood vessels improves the delivery of nanomedicines in a size-dependent manner", Nature Nanotechnol, 7:383-8 (2012).
Choi, et al., "Design Considerations for Tumor-Targeted Nanoparticles", Nature Nanotechnol, 5, 42-7 (2010).

(Continued)

*Primary Examiner* — Jeanette M Lieb
(74) *Attorney, Agent, or Firm* — Pabst Patent Group LLP

(57) ABSTRACT

A protein nanocage formulation with enhanced mucus penetration capability and colloidal stability provides controlled delivery of therapeutic, prophylactic, or diagnostic agents to tumors. A dense coating of a surface altering agent such as polyethylene glycol on self-assembled protein nanocages enhances the rapid and uniform distribution of the formulation at mucosal tissues following topical administration, enhances circulation time following intravenous administration, and enhances penetration into hypoxic tumor cores. The density and the molecular weight of surface altering agents are selected to allow the protein nanocages to also bind to tumor cell receptors and release chemotherapeutic agents after tumor cell uptake. Agents delivered in the formulation have better efficacy compared to carrier-free agents. A method of making the protein nanocage formulation with enhanced mucus penetration and colloidal stability is also provided.

19 Claims, 8 Drawing Sheets

Specification includes a Sequence Listing.

(56) References Cited

OTHER PUBLICATIONS

Fan, et al., "Magnetoferritin nanoparticles for targeting and visualizing tumour tissues", Nat Nanotechnol, 7:459-64 (2012).
Guo, et at., "All-trans retinol, vitamin D and other hydrophobic compounds bind in the axial pore of the five-stranded coiled-coil domain of cartilage oligomeric matrix protein", EMBO J., 17: 5265-72 (1998).
Ham, et al., "Apoferritin-based nanomedicine platform for drug delivery: equilibrium binding study of daunomycin with DNA", J Mater Chem, 21:8700-8 (2011).
Harris, et al., "Effect of pegylation on pharmaceuticals", Nat Rev Drug Discov, 2:214-21 (2003).
Huang, et al., "Protein nanocages that penetrate airway mucus and tumor tissue", Proceedings National Academy of Sciences, 114(32):E6595-E6602 (2017).
Huang, et al., "The Effect of Injection Routes on the Biodistribution, Clearance and Tumor Uptake of Carbon Dots", ACS Nano, 7, 5684-93 (2013).
Kukulj, et al., "Altered iron metabolism, inflammation, transferrin receptors, and ferritin expression in non-small-cell lung cancer", Med Oncol, 27:268-77 (2010).
Lee, et al., "Three-dimensional culture models of normal and malignant breast epithelial cells", Nature Methods, 4:359-65 (2007).
Lin, et al., "Preparation, characterization and uptake of PEG-coated, muco-inert nanoparticles in HGC-27 cells, a mucin-producing, gastric-cancer cell line". J Biomedl Nanotechnol, 9(12):2017-23 (2013).
Maham, et al, "Protein-based nanomedicine platforms for drug delivery", Small, 5:1706-21 (2009).
Malashkevich, et al., "The crystal structure of a five-stranded coiled coil in COMP: a prototype ion channel", Science, 274:761-5 (1996).
Mastorakos, et al., "Highly compacted biodegradable DNA nanoparticles capable of overcoming the mucus barrier for inhaled lung gene therapy", PNAS, 112(28):8720-5 (2015).
Minchinton, et al., "Drug penetration in solid tumours", Nat Rev Cancer, 6:583-92 (2006).
Murata, et al., "Design and Function of Engineered Protein Nanocages as a Drug Delivery System for Targeting Pancreatic Cancer Cells via Neuropilin-1", Mol. Pharm, 12(5):1422-30 (2015).
Nance, et al., "Brain-penetrating nanoparticles improve paclitaxel efficacy in malignant glioma following local administration", ACS Nano, 8:10655-64 (2014).
Ren, et al., "Engineered drug-protein nanoparticle complexes for folate recptor targeting", Biochemical Engineering Journal, 89:33-41 (2013).
Ruoslahti, et al., "Specialization of tumour vasculature", Nat. Rev. Cancer, 2:83-90 (2002).
Wang, et al, "A nanoparticle-based strategy for the imaging of a broad range of tumours by nonlinear amplification of microenvironment signals", Nat Mater, 13:204-12 (2014).
Zhang and Orner, "Self-assembly in the ferritin nano-cage protein superfamily", Int. J. Mol. Sci., 12:5406-21 (2011).
Zhu, et al, "RGD-modified PEG-PAMAM-DOX conjugate: in vitro and in vivo targeting to both tumor neovascular endothelial cells and tumor cells", Adv Mater, 23:H84-9 (2011).
International Search Report PCT/US2017/052079 dated Feb. 2, 2018.
Ceci, et al., "Selective targeting of melanoma by PEG-masked protein-based multifunctional nanoparticles", Int. J. Nanomed., 1489-1509 (2012).

* cited by examiner

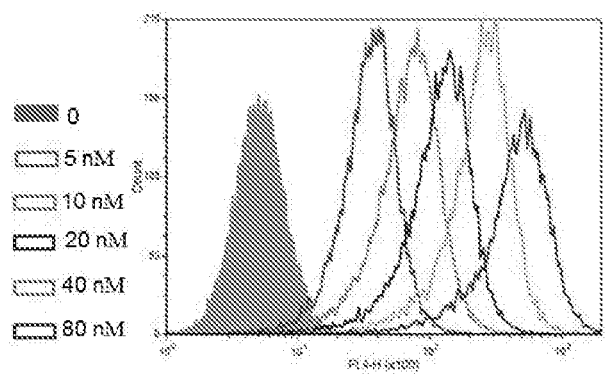
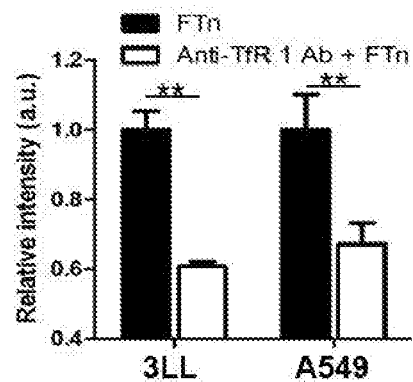
FIG. 3A
FIG. 3B
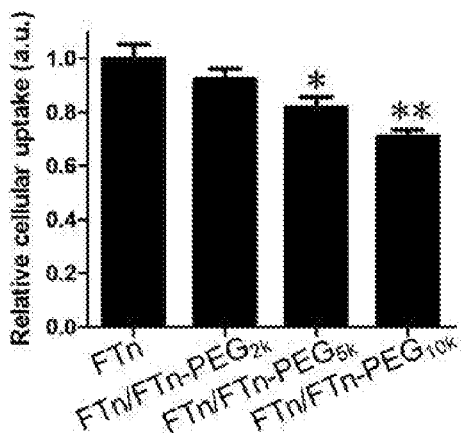
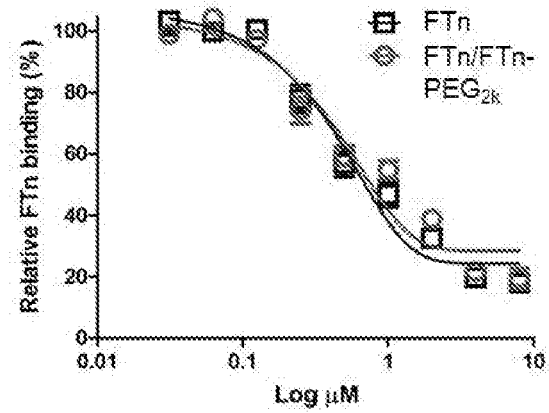
FIG. 3C
FIG. 3D

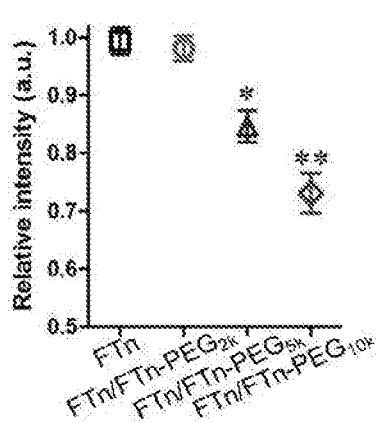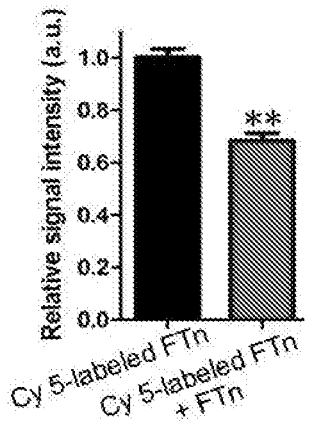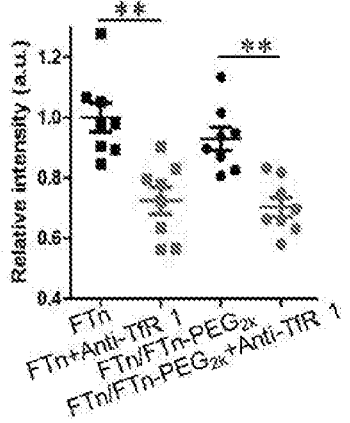
FIG. 4A          FIG. 4B          FIG. 4C
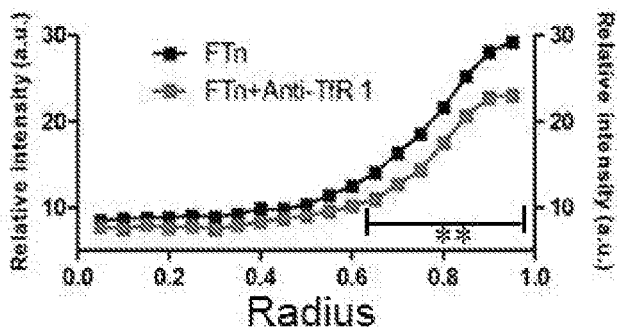
FIG. 4D
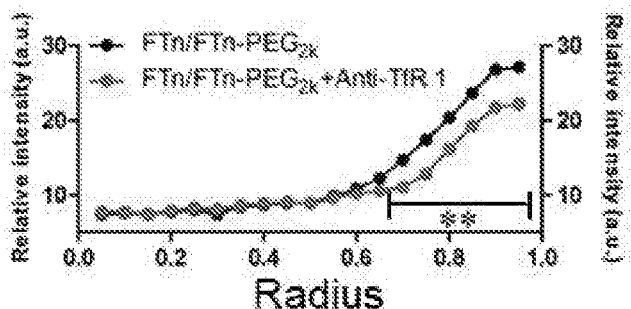
FIG. 4E

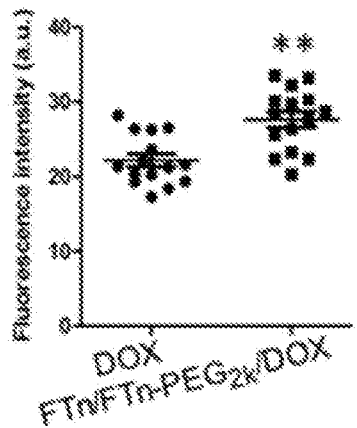 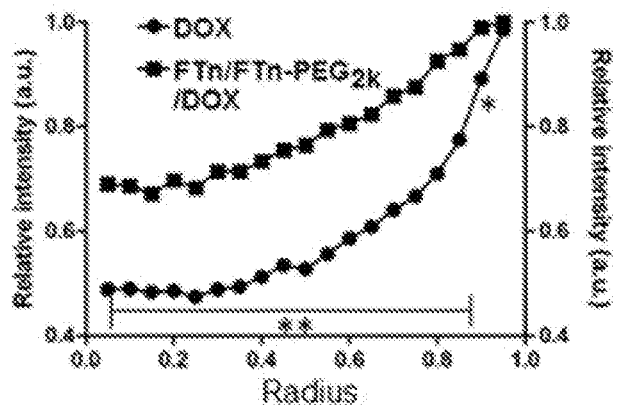
FIG. 6A  FIG. 6B
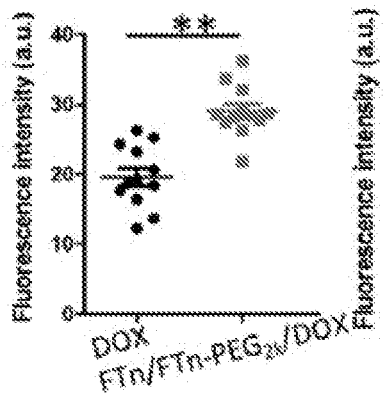 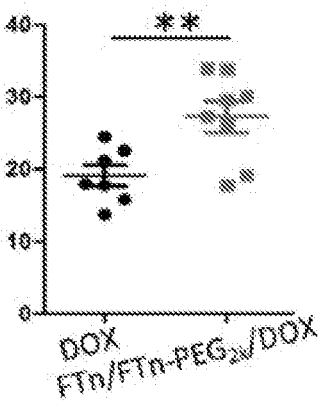 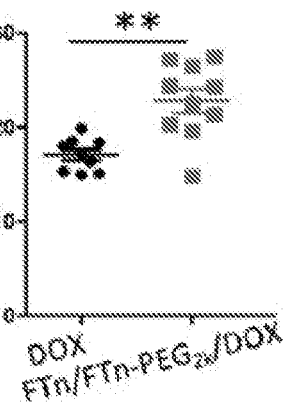
FIG. 6C  FIG. 6D  FIG. 6E
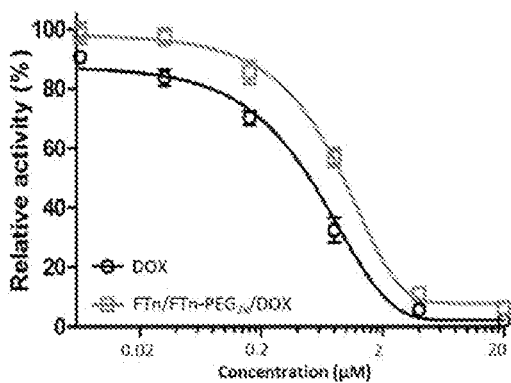 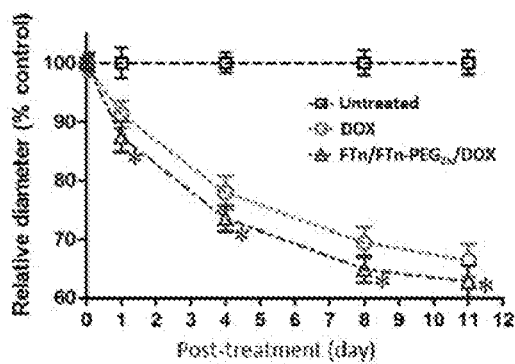
FIG. 6F  FIG. 6G

SEQUENCE LISTING

```
<160> NUMBER OF SEQ ID NOS: 6

<210> SEQ ID NO 1
<211> LENGTH: 183
<212> TYPE: PRT
<213> ORGANISM: Homo sapiens

<400> SEQUENCE: 1

Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
            20                  25                  30

Tyr Val Tyr Leu Ser Met Ser Tyr Tyr Phe Asp Arg Asp Asp Val Ala
        35                  40                  45

Leu Lys Asn Phe Ala Lys Tyr Phe Leu His Gln Ser His Glu Glu Arg
    50                  55                  60

Glu His Ala Glu Lys Leu Met Lys Leu Gln Asn Gln Arg Gly Gly Arg
65                  70                  75                  80
```

Ile Phe Leu Gln Asp Ile Lys Lys Pro Asp Cys Asp Trp Glu Ser
                85                  90                  95

Gly Leu Asn Ala Met Glu Cys Ala Leu His Leu Glu Lys Asn Val Asn
            100                 105                 110

Gln Ser Leu Leu Glu Leu His Lys Leu Ala Thr Asp Lys Asn Asp Pro
        115                 120                 125

His Leu Cys Asp Phe Ile Glu Thr His Tyr Leu Asn Glu Gln Val Lys
130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                165                 170                 175

Gly Asp Ser Asp Asn Glu Ser
            180

<210> SEQ ID NO 2
<211> LENGTH: 178
<212> TYPE: PRT
<213> ORGANISM: Artificial Sequence
<220> FEATURE:
<223> OTHER INFORMATION: Synthetic Peptide

<400> SEQUENCE: 2

Thr Ser Gln Val Arg Gln Asn Tyr His Gln Asp Ser Glu Ala Ala Ile
1               5                   10                  15

Asn Arg Gln Ile Asn Leu Glu Leu Tyr Ala Ser Tyr Val Tyr Leu Ser
            20                  25                  30

Met Ser Tyr Tyr Phe Asp Arg Asp Asp Val Ala Leu Lys Asn Phe Ala
        35                  40                  45

Lys Tyr Phe Leu His Gln Ser His Glu Glu Arg Glu His Ala Glu Lys
50                  55                  60

Leu Met Lys Leu Gln Asn Gln Arg Gly Gly Arg Ile Phe Leu Gln Asp
65                  70                  75                  80

Ile Lys Lys Pro Asp Cys Asp Asp Trp Glu Ser Gly Leu Asn Ala Met
                85                  90                  95

Glu Cys Ala Leu His Leu Glu Lys Asn Val Asn Gln Ser Leu Leu Glu
            100                 105                 110

Leu His Lys Leu Ala Thr Asp Lys Asn Asp Pro His Leu Cys Asp Phe
        115                 120                 125

Ile Glu Thr His Tyr Leu Asn Glu Gln Val Lys Ala Ile Lys Glu Leu
130                 135                 140

Gly Asp His Val Thr Asn Leu Arg Lys Met Gly Ala Pro Glu Ser Gly
145                 150                 155                 160

Leu Ala Glu Tyr Leu Phe Asp Lys His Thr Leu Gly Asp Ser Asp Asn
                165                 170                 175

Glu Ser

<210> SEQ ID NO 3
<211> LENGTH: 27
<212> TYPE: DNA
<213> ORGANISM: Artificial Sequence
<220> FEATURE:
<223> OTHER INFORMATION: Synthetic Primer

<400> SEQUENCE: 3
cgccatatga cgaccgcgtc cacctcg                                    27

```
<210> SEQ ID NO 4
<211> LENGTH: 39
<212> TYPE: DNA
<213> ORGANISM: Artificial Sequence
<220> FEATURE:
<223> OTHER INFORMATION: Synthetic Primer

<400> SEQUENCE: 4
ccgctcgagt tagctttcat tatcactgtc tcccagggt                    39

<210> SEQ ID NO 5
<211> LENGTH: 41
<212> TYPE: DNA
<213> ORGANISM: Artificial Sequence
<220> FEATURE:
<223> OTHER INFORMATION: Synthetic Primer

<400> SEQUENCE: 5
cgccatatga tggaagatgc caaaaacatt aagaagggcc c                 41

<210> SEQ ID NO 6
<211> LENGTH: 29
<212> TYPE: DNA
<213> ORGANISM: Artificial Sequence
<220> FEATURE:
<223> OTHER INFORMATION: Synthetic Primer

<400> SEQUENCE: 6
cgggatccca cggcgatctt gccgccctt                               29
```

PROTEIN NANOCAGES WITH ENHANCED MUCUS PENETRATION FOR TARGETED TISSUE AND INTRACELLULAR DELIVERY

CROSS-REFERENCE TO RELATED APPLICATIONS

This application is a National Phase application under 35 U.S.C. 371 of PCT/US2017/052079, filed Sep. 18, 2017, which claims the benefit of and priority to U.S. Application No. 62/395,852, filed Sep. 16, 2016, which are incorporated herein by reference in their entirety.

REFERENCE TO SEQUENCE LISTING

The Sequence Listing submitted Sep. 18, 2017, as a text file named "JHU_C_14289_PCT_ST25.txt," created on Sep. 18, 2017, and having a size of 4,389 bytes is hereby incorporated by reference.

STATEMENT REGARDING FEDERALLY SPONSORED RESEARCH OR DEVELOPMENT

This invention was made with government support under CA151838, HL127413, EY001765, and HL136617 awarded by the National Institutes of Health. The government has certain rights in the invention.

FIELD OF THE INVENTION

The present invention relates to the field of protein-based drug delivery systems to treat disease, and more particularly, to delivery systems for chemotherapeutic agents for treatment of tumors, including those adjacent to or within mucosal tissues.

BACKGROUND OF THE INVENTION

Lung cancer and other cancers of tissues having mucosal surfaces present serious challenges to effective diagnosis and treatment. Lung cancer is the leading cause of cancer-related deaths in the United States and worldwide. Of the multiple types of lung cancer, small-cell lung cancer (SCLC) and squamous-cell lung cancer predominantly present in the conducting airways, which encompass at least 45% of all lung cancer cases (Herbst R S, et al., *The New England Journal of Medicine*, 359:1367-1380 (2008)). Barriers to more effective cancer therapy include rapid mucociliary clearance (MCC) by the mucus gel layer lining the mucosa for mucosal delivery, instability and clearance in systemic circulation, lack of tumor cell-specific uptake, insufficient penetration into and throughout the tumor tissue, and inability to selectively target tumor versus healthy tissue (Oh P, et al., *Nature Medicine*, 20:1062:1068 (2014)).

The protective mucus layer lining the mucosal epithelium is a dense network of highly adhesive macromolecules that traps most particulate matter, leading to its elimination from the lungs by MCC (Kim N, et al., *J Control Release*, Epub May 16, 2016; Suk J S, et al., *Advanced Drug Delivery Reviews*). Muco-inert particulate formations showed promises in delivering vehicles across mucus by reducing hydrophobic or electrostatic interactions between the particulates and mucin fibers (Lin D, et al., *Journal of Biomedical Nanotechnology*, 9(12):2017-23 (2013)). However, these particles do not specifically target tumor cells, much less penetrate tumor tissues.

Protein and polypeptide-based nanostructures provide an attractive platform for cancer targeted delivery. Various tumors express surface markers (e.g., specific receptors and integrins), and therefore protein/peptide-based targeting ligands are used to impart tumor specificity in nanostructures. However, overcoming delivery route barriers (e.g., mucus, instability in blood), specific targeting at tumor tissues, and intracellular release of cytotoxic agents are challenging.

For example, US2015/0224212 to Park et al describes an Archaea-derived protein capable of forming nanocages and encapsulating metal ions. Park et al requires conjugation of an antibody or epitope to impart the targeting effect at an upregulated antigen in tumor cells. It lacks any surface modification to effect mucus penetration or to overcome delivery route barriers. Vannucci L, et al., *International Journal of Nanomedicine*, 7:1489-1509 (2012) requires arginine-glycine-aspartate (RGD)-containing tumor targeting peptide on the surface of protein-based nanoparticles, and utilizes polyethylene glycol (PEG) to mask the protein from its physiological receptors. However, its PEG density is insufficient to impart mucus penetration capability. The PEG is conjugated to the protein forming the nanoparticles via thiol-containing amino acids, which have a limited quantity and therefore results in a low surface density of PEG. Consequently, the nanoparticles require tumor-targeting ligands to effect tumor specificity.

Therefore, it is an object of the present invention to provide mucus-penetrating, tumor-targeting nanostructure formulations to overcome delivery route barriers, penetrate tumor tissues, and allow for accurate intracellular delivery of a wide range of drugs at tumor site.

It is another object of the present invention to provide methods of preparing and using these nanostructure formulations with versatile functionalities and using them in the treatment and diagnostic of tumors.

SUMMARY OF THE INVENTION

A protein nanocage has been developed for delivery of therapeutic or diagnostic agents to penetrate both tumor tissues and the mucus layer. Protein nanocages are formed from the assembly of proteins or peptides that may have cancer-targeting ability. The surface of protein nanocages is associated with a surface altering agent, preferably as a coating, where the surface altering agent may include a polyalkylene oxide at a density effective to impart mucus penetration capability, yet maintains the cancer-targeting property of protein nanocages. The protein nanocages further incorporate one or more therapeutic, prophylactic or diagnostic agents by encapsulation in the cavity of the structure or by covalent linkage. The formulation preferably is formed with material generally recognized as safe by the Food and Drug Administration ("GRAS"), and the self-assembling proteins are preferably natural or recombinantly produced mammalian proteins. In one embodiment, the protein is native human ferritin heavy chain or recombinantly produced protein with at least 80%, 85%, or 90% homology to the native molecule. Ferritin heavy-chain proteins self-assemble at a neutral, or near neutral physiological pH, into roughly spherical nano-sized structures each with an internal cavity, denoted as ferritin heavy-chain nanocages (FTn). Surface altering agents including polyalkylene oxides, preferably polyethylene glycol (PEG), are bound to the self-assembling proteins or the formed nanocages, forming a coating enhancing the colloidal stability of nanocages in bodily fluids. Particularly, coated protein nanocages with a surface altering agent of selected molecular weight and/or surface coating density result in wide coverage at mucosal tissues, e.g., upon inhalation of the formulation. In a preferred embodiment, ferritin heavy-chain proteins are modified at a high degree of modification with PEG (e.g., more than four PEG per ferritin heavy chain) are used to form mucus penetrating and colloidally-stable ferritin nanocages, leading to a dense coating of PEG between about 10 and about 50 PEG/100 $nm^2$ on the surface of formed nanocages. Preferably, the surface altering agents form a brush conformation on the surface of the protein nanocages. With surface altering agents of carefully a selected molecular weight, the coating does not prevent the protein nanocages from targeting tumor tissues, for example, by binding to receptors on tumor cells. Polyalkylene oxides of molecular weights between 300 Da and 100 kDa can be used to enable mucus penetration of ferritin nanocages. In a preferred embodiment, the PEG has a molecular weight of greater than 300 Daltons and less than or equal to about 5 kDa, for example, more preferably 2 kDa, which allows the nanocages to bind to and be taken up selectively by cancer cells but not normal cells.

The nanocage formulation with a dense coating of the surface altering agent is capable of efficiently penetrating tumor tissues, including hypoxic tumor cores, following local or systemic administration; and selectively enters cancer cells, e.g., in a transferrin receptor 1-dependent manner for a formulation containing FTn. Ferritin proteins have selective affinity to transferrin receptor 1 (TfR 1). Unlike conventional PEGylation methods that often compromise intrinsic functionalities of core protein (Harris J M, et al., *Nat Rev Drug Discov,* 2:214-221 (2003)), the drug-loaded, pegylated protein nanocages are formed via a "hybrid" strategy which does not affect the ability of FTn to selectively interact with and internalize into cancer cells. Generally, a hybrid protein nanocage contains two or more of the following units in an assembled form: self-assembling protein or peptide, self-assembling protein or peptide which is conjugated with a surface altering agent, and self-assembling protein or peptide which is associated with a therapeutic or imaging agent. A "hybrid" strategy uses strong acidic or basic pH and/or urea to dissemble any "homogeneous" protein nanocages into "monomeric" units, and a mixture of different compositions of "monomeric" units can re-assemble to form a hybrid protein nanocage when incubated in a neutral or near neutral medium and/or in a medium devoid of urea or with urea being sustantially removed.

A wide array of chemotherapeutic or diagnostic agents can be loaded via chemical conjugation and/or physical entrapment without perturbing the payloads' intrinsic characteristics and the capabilities of the protein nanocages to overcome delivery barriers such as mucus, actively target and penetrate tumor tissues, and release payload upon tumor cell uptake. For example, chemotherapeutic agents can be covalently bound to the protein nanocages via an acid-sensitive linker which is cleaved upon tumor cell uptake of protein nanocages. This avoids drug release prior to uptake by cancer cells.

The protein nanocages coated with a surface altering agent can be formulated in a formulation containing pharmaceutically acceptable excipients in a medium with an appropriate pH, e.g., between pH 4 and pH 9, preferably between pH 5 and pH 8, more preferably between pH 6 and pH 7.5. In some embodiments, the formulation containing coated protein nanocages with a surface altering agent is free of, or essentially free of, urea or any other denaturing molecules for proteins.

The protein nanocage, or its formulation, leads to significantly enhanced anti-cancer efficacy compared to dose-matched, carrier-free chemotherapeutic drugs, for example, more than 50%, 55%, or 60% survival 60 days after treatment compared to only 18 days of survival in animals treated with an equivalent dose of carrier free drugs, in an invasive lung cancer in vivo following inhalation administration. It also efficiently partitioned into tumor tissue following systemic administration beyond the level achieved by protein nanocages without the mucus penetration enhancing coating.

A method to form mucus penetrating protein nanocages uses self-assembly, disassembly and reassembly at different environments (e.g., pH and concentration of urea). Particularly, a "hybrid" strategy is used, which does not affect the ability of FTn to selectively interact with and internalize into cancer cells. Protein or peptide molecules with different modifications (e.g., associated with surface altering agents, associated with therapeutic agents, or labeled with imaging agents) can be mixed at user-selected ratios for processing into hybrid nanocages. A plurality of self-assembling proteins or their assembled nanocages, at least 25%, 30%, 40%, or 50% of the plurality containing mucus penetration enhancing materials, are mixed in a solution. Adjusting the pH to strong acidity (e.g., pH 2) or basicity, and/or adding urea, dissemble existing protein nanocages. Further adjustment of the pH of the solution to neutrality or to a near neutral pH, and/or removal of urea, supports the formation of hybrid mucus penetrating protein nanocages, where each nanocage contains two or more of the following self-assembling units: ferritin protein or its analog with at least 80% homology, ferritin protein or its analog that is conjugated with a surface altering agent, ferritin protein or its analog that is associated with a therapeutic or imaging agent.

In some embodiments, the protein nanocage with one or more therapeutic agent incorporated or chemically linked is used as a stand-alone therapy for patients with tumors. In other embodiments, the protein nanocage in a suitable formulation is used as an adjuvant therapy combined with systemic chemo- or immunotherapy.

BRIEF DESCRIPTION OF THE DRAWINGS

FIGS. 1A-1D show the assembly, disassembly, and reassembly process of ferritin nanocages (FTn) and surface-modified, hybrid FTn. FIG. 1A is a schematic of FTn disassembly at low pH and reassembly at neutral pH. FIG. 1B is a line graph showing the absorbances at 280 nm of FTn at pH 7.4 and FTn at pH 2.0 over retention time (min) in size exclusion chromatography. FIG. 1C is a schematic of the assembly of hybrid FTn formulated with Alexa Fluor® 488 (AF488)-conjugated FTn (FTn-AF 488) and poly(ethylene glycol) (PEG)-conjugated FTn (FTn-PEG) by controlling pH. FIG. 1D is a schematic of the assembly of hybrid FTn formulated with non-modified FTn, AF488-FTn, and PEG(2 kDa)-FTn.

FIGS. 2A-2D show the effects of proportion (density, %) and molecular weights of PEGylated ferritin protein on the targeting and mucosal penetration capabilities of FTn. FIG. 2A is a line graph of the relative uptake (%) of FTn by Lewis lung carcinoma (3LL) cells over FTn formed with varying density (%) of 2 kDa PEG. The uptake of non-PEGylated FTn is considered 100%. FIG. 2B is a bar graph of the relative intensity of a fluorescence dye, Cy5-labeled FTn in the 3D tumor spheroids over the density (%) of 2 kDa PEGylated ferritin in the composition of FTn. FIGS. 2C and 2D are bar graphs of the epithelial coverage area (%) and the total fluorescence intensity distributed throughout mouse airways, respectively, by FTn formulated without PEG, with 2 kDa PEG, 5 kDa PEG, or 10 kDa PEGylated ferritin. (mean±SEM; ** $p<0.01$ compared to the non-PEGylated FTn).

FIGS. 3A-3D show the specific uptake of non-PEGylated or PEGylated FTn via transferrin receptor 1 (TfR 1) in various cancer cell lines. FIG. 3A is a flow cytometry diagram showing counts over intensities of fluorescently positive cells that were treated with Cy 5-labeled, non-PEGylated FTn at 0, 5, 10, 20, 40, and 80 nM. FIG. 3B is a bar graph showing the relative intensity of binding of Cy 5-labeled FTn to 3LL cells or A549 cells in the absence or presence of anti-TfR 1 Ab. FIG. 3C is a bar graph of relative cellular uptake of FTn formed with non-PEGylated ferritin or ferritin PEGylated with 2, 5, or 10 kDa. (*$p<0.05$, ** $p<0.01$ compared to non-PEGylated FTn). FIG. 3D is a line graph of relative binding of Cy 5-labeled FTn to 3LL cells at different concentrations of non-PEGylated FTn (FTn) or FTn formed with PEG2k-ylated ferritin (FTn/FTn-PEG$_{2k}$).

FIGS. 4A-4G show deep penetration of PEGylated FTn throughout tumor tissues. FIG. 4A is a dot plot showing the mean Cy 5 fluorescence signal intensity in the whole 3D-constructed cell spheroids that were penetrated by Cy 5-labeled FTn formed with non-PEGylated ferritin, 50% PEG2k-ylated ferritin, 50% PEG5k-ylated ferritin, or 50% PEG10k-ylated ferritin. (n≥8 cell spheroids per group; *$p<0.05$, ** $p<0.01$ compared to non-PEGylated FTn.) FIG. 4B is a bar graph of relative fluorescence signal intensity in tumor spheroids penetrated by Cy 5-labeled FTn in the absence or presence of excess amounts of unlabeled FTn. FIG. 4C is a dot plot of the relative fluorescence intensity in tumor spheroids that were penetrated by FTn or FTn/FTn-PEG$_{2k}$ in the absence or presence of a 10-fold molar excess of anti-TfR 1 antibody. FIG. 4D is a line graph of the relative fluorescence intensity over the relative radius in the middle section of tumor spheroids. Spheroids were penetrated by FTn in the absence or presence of anti-TfR 1 antibody. Radius=0 and 1 indicate the center and edge of the tumor spheroid, respectively. FIG. 4E is a line graph of the relative fluorescence intensity over the relative radius in the middle section of tumor spheroids. Spheroids were penetrated by FTn/FTn-PEG$_{2k}$ in the absence or presence of anti-TfR 1 antibody. Radius=0 and 1 indicate the center and edge of the tumor spheroid, respectively. FIG. 4F is a bar graph of the relative amount of TfR-1 expression in proximal lung, distal lung, and subcutaneous 3LL-based tumor tissues. FIG. 4G is a bar graph of the relative amount of TfR-1 expression in proximal lung, distal lung, and orthotopic 3LL-based lung cancer tissues.

FIG. 5A is a schematic illustration of the synthesis of PEGylated FTn conjugated with doxorubicin (DOX) via an acid-sensitive linker. FIG. 5B is a line graph of relative release (%) of DOX from DOX-conjugated, PEGylated FTn over time (day) in pH 7.4 and pH 5.0.

FIG. 6A is a dot plot of the mean fluorescence intensity throughout 3LL-based spheroids that were incubated with free DOX or DOX-conjugated, PEGylated FTn (FTn/FTn-PEG$_{2k}$/DOX). (DOX autofluoresces.) FIG. 6B is a line graph of the relative fluorescence intensity over the relative radius in the middle section of tumor spheroids, where the spheroids were incubated with free DOX or FTn/FTn-PEG$_{2k}$/DOX. FIGS. 6C-6E are dot plots of the mean fluorescence intensities throughout A549-based spheroids (6C), H1975-based spheroids (6D), and H460-based spheroids (6E), respectively, after incubation with free DOX or FTn/FTn-PEG$_{2k}$/DOX. FIG. 6F is a line graph of the relative remaining activity (%) of 3LL cells over the concentration (μM) of free DOX or FTn/FTn-PEG$_{2k}$/DOX after incubation for 24 hours. FIG. 6G is a line graph of the relative average diameter (%, relative to untreated control at each time points) of 3LL-based spheroids over time (day) after treatment with free DOX or FTn/FTn-PEG$_{2k}$/DOX. (n≥20 cell spheroids (±SEM); *$p<0.05$ compared to free DOX).

FIG. 7A is a dot plot of bioluminescence signal intensity of 3LL-Luciferase-based orthotopic proximal lung cancer in mice that were untreated or treated with intratreacheally administered free DOX or FTn/FTn-PEG$_{2k}$/DOX over time (day). FIG. 7B is a line graph showing Kaplan-Meier survival curves (survival percentage, %, over time, day) for mice having 3LL-based orthotopic proximal lung cancer that were untreated or treated one dose with intratreacheally administered free DOX or FTn/FTn-PEG$_{2k}$/DOX.

DETAILED DESCRIPTION OF THE INVENTION

I. Definitions

Figure 1A:
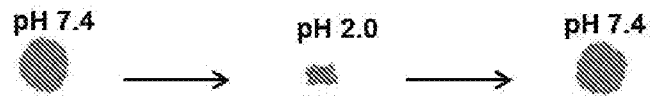

The term "self-assembling" refers to the capability of molecules to spontaneous assemble, or organize, to form multimers or a high ordered structure in a suitable environment.

The term "nanocage" refers to a nanoparticle with an internal cavity or a hollow nanoparticle.

As used herein, the term "active agent" or "biologically active agent" are used interchangeably herein to refer to a chemical or biological compound that induces a desired pharmacological and/or physiological effect, which may be prophylactic, therapeutic or diagnostic. The terms also encompass pharmaceutically acceptable, pharmacologically active derivatives of active agents, including, but not limited to, salts, esters, amides, prodrugs, active metabolites, and analogs.

The term "therapeutic agent" refers to an agent that can be administered to prevent or treat one or more symptoms of a disease or disorder.

The term "diagnostic agent", as used herein, generally refers to an agent that can be administered for purposes of identification or imaging.

The term "prophylactic agent", as used herein, generally refers to an agent that can be administered to prevent disease or to prevent certain conditions like pregnancy.

The phrase "pharmaceutically acceptable" refers to compounds, excipients, formulations or agents which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" refers to pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient.

The phrase "therapeutically effective amount" refers to an amount of the therapeutic agent that produces some desired effect at a reasonable benefit/risk ratio applicable to any medical treatment. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation. A prophylactic agent refers to an agent that may prevent a disorder, disease or condition. Examples include vaccines which prevent infection and birth control pills that prevent pregnancy.

The term "treating" refers to preventing or alleviating one or more symptoms of a disease, disorder or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

The term "biocompatible" as used herein, generally refers to materials that are, along with any metabolites or degradation products thereof, generally non-toxic to the recipient, and do not cause any significant adverse effects to the recipient. Generally speaking, biocompatible materials are materials which do not elicit a significant inflammatory or immune response when administered to a patient.

The term "biodegradable" as used herein, generally refers to a material that will degrade or erode under physiologic conditions to smaller units or chemical species that are capable of being metabolized, eliminated, or excreted by the subject. The degradation time is a function of composition and morphology. Degradation times can be from hours to years.

The term "external stimulus", as used herein, evokes a specific functional reaction, which is not intrinsic, such as a physical, chemical, biological, mechanical, and irradiation stimuli.

"Physiological", as used herein, refers to conditions found in living vertebrates. In particular, physiological conditions refer to the conditions in the human body such as temperature, pH, aqueous medium, etc. "Physiological temperatures", as used herein, refers to a temperature range of between 35° C. to 42° C., preferably around 37° C.

II. Mucus Penetrating Protein Nanocages with Tumor Specificity

A. Proteins with Specificity and Assembly Modules

Ferritin family proteins may be used in the formulation as the tumor-targeting basis for protein-based nanostructures. They have intrinsic and selective affinity to markers on the surface of tumor cells, such as the transferrin receptor 1 (TfR 1) which is highly expressed on rapidly dividing tumor cells (Li L, et al., *Proc Nat Acad Sci*, 107:3505-3510 (2010); Fan K, et al., *Nature Nanotechnology*, 7:459-464 (2012); Kukulj S, et al., *Med Oncol*, 27:268-277 (2010)). Ferritin is the primary iron transport and storage protein in both prokaryotes and eukaryotes. It is composed of 24 subunits of the ferritin heavy and light chains each. The subunits self-assemble into a cage-like structure that possesses an internal cavity, capable of accommodating therapeutic and/or diagnostic agents. Members of the ferritin family can self-assemble into cage architectures with a roughly spherical and hollow structure. Maxi-ferritins form hollow spheres with octahedral symmetry composed of twenty-four monomers. Mini-ferritins are tetrahedrally symmetric, hollow assemblies composed of twelve monomers. Maxi-ferritins are composed of twenty-four identical or homologous subunits (~20 kDa) that assemble into a large spherical cage (outer diameter~120 Å) with a hollow cavity (inner diameter~80 Å). The size of ferritin nanocages is smaller than that required to facilitate delivery of payloads through nanoporous tissue barriers, including interstitial tissues (Barua S, et al, *Nano Today*, 9:223-243 (2014)) and poorly permeable tumors (Cabral H, et al, *Nature nanotechnology*, 6:815-823 (2011)). Mammalian ferritins often consist of two types of similar subunits, heavy (H) and light (L) chain, with a molecular weight of approximately 21 and approximately 19 kDa respectively. (Zhang Y and Omer B P, *Int. J. Mol. Sci.*, 12:5406-5421 (2011))

Changing the pH can change key electrostatic forces in the interactions among subunits. At physiological pH, ferritin exists as a stable 24-mer, while in highly acidic or basic solutions it disassembles. This spontaneously reassembles when returned to a neutral solution.

Recombinant human ferritin proteins are preferred due to lower risks of immunogenicity. In a preferred embodiment, the subunit in forming the protein nanocages has at least 80, 85, 90, 95, 99, or 100 percent sequence identity to that of human native ferritin heavy chain:

```
                                           (SEQ ID: 1)
MTTASTSQVR QNYHQDSEAA INRQINLELY ASYVYLSMSY

YPDRDDVALK NFAKYFLHQS HEEREHAEKL MKLQNQRGGR

IFLQDIKKPD CDDWESGLNA MECALHLEKN VNQSLLELHK

LATDKNDPHL CDFIETHYLN EQVKAIKELG DHVTNLRKMG

APESGLAEYL FDKHTLGDSD NES.
```

In some embodiments, the subunit in forming ferritin naoncages has at least 80, 85, 90, 95, 99, or 100 percent similarity in sequence identity to an engineered ferritin heavy chain:

```
                                           (SEQ ID: 2)
TSQVRQNYHQDSEAAINRQINLELYASYVYLSMSYYFDRDDVALKN

FAKYFLHQSHEEREHAEKLMKLQNQRGGRIFLQDIKKPDCDDWESG

LNAMECALHLEKNVNQSLLELHKLATDKNDPHLCDFIETHYLNEQV

KAIKELGDHVTNLRKMGAPESGLAEYLFDKHTLGDSDNES.
```

Underlined amino acids contained primary amines (—NH$_2$) for PEGylation and/or fluorescence dye conjugation. Each subunit of FTn include fourteen—NH$_2$.

Other proteins capable of assembly into particulate nanostructures can be used instead of ferritin. For example, naturally occurring heat shock protein (HSP) cages modified with cancer cell targeting peptides such as neuropilin 1-binding peptide (Murata M, et al., *Mol. Pharmaceutics*, 12(5):1422-1430 (2015)) can be modified with surface altering agents with selected density and molecular weight to effect mucus penetration, tumor tissue penetration, and uptake by cancer cell.

Other examples include multimerizable protein domains including coiled-coil domains. The coiled coil domain may be derived from laminin Coiled coil domains may also be derived from the thrombospondins in which three (TSP-1 and TSP-2) or five (TSP-3, TSP-4 and TSP-5) chains are connected, or from COMP (COMPcc) (Guo, et at., *EMBO J.*, 1998, 17: 5265-5272) which folds into a parallel five-stranded coiled coil (Malashkevich, et al., *Science*, 274: 761-765 (1996)). These domains can also be linked or fused with tumor targeting molecules. Surface altering agents such as polyalkylene oxide can be further modified on to some or all of these multimerizable domains, forming mucus penetrating protein-based nanostructures with tumor specificity.

B. Materials that Enhance Particle Diffusion Through Mucus

The proteins forming the nanocages preferably have bound thereto a surface altering agent or material that as a coating enhances the mobility, diffusion, or penetration through mucus of coated nanoparticulates including protein nanocages. This type of surface altering agent or material is also referred to as a mucus penetration enhancing material. It is an agent or material which modifies one or more properties of the particles for the surface, including, but not limited to, hydrophilicity (e.g., makes the nanocages more or less hydrophilic), surface charge (e.g., makes the surface neutral or near neutral between about −10 mV and about +10 mV, or more negative or positive), and/or enhances transport in or through bodily fluids and/or tissues, such as mucus and circulation. In some embodiments, the surface-alternating material provides a direct therapeutic effect, such as reducing inflammation.

Examples of the surface-altering agents include, but are not limited to, polyalkylenes such as polyethylene and polypropylene and derivatives therein (referred to collectively as polyalkylenes, unless otherwise designated), polyalkylene glycols such as poly(ethylene glycol) (PEG), polyalkylene oxides (PEO), copolymers of polyalkylenes (e.g., copolymer of PEG) and derivatives thereof, proteins such as anionic proteins like albumin, surfactants, and sugars or sugar derivatives (e.g., cyclodextrin). Preferred surface-altering agents are polyethylene glycols, polyalkylene oxides, heparin and poloxomers (polyethylene oxide block copolymers such as the PLURONICS® marketed by BASF, for example, F127).

A particularly material is PEG. Representative PEG molecular weights include 300 Da, 600 Da, 1 kDa, 2 kDa, 3 kDa, 4 kDa, 5 kDa, 6 kDa, 8 kDa, 10 kDa, 15 kDa, 20 kDa, 30 kDa, 50 kDa, 100 kDa, 200 kDa, 500 kDa, and 1 MDa and all values within the range of 300 Daltons to 1 MDa. In more preferred embodiments, the PEG is a linear molecule with a molecular weight of less than 5 kDa (e.g., 2 kDa, 1 kDa, 600 Da, 300 Da). In other embodiments, the PEG is a branched molecule with a molecular weight of less than 5 kDa in each branch (e.g., 2 kDa). PEG of any given molecular weight may vary in other characteristics such as length, density, and branching.

In one embodiment, the surface altering agents such as PEG are chemically bound or physically adsorbed to the proteins forming the nanocages or the proteins are recombinantly produced with surface-modifying proteins or peptides. In another embodiment, the proteins are chemically linked, physically adsorbed to the assembled protein nanocages.

Surface density and molecular weight of surface altering agents such as poly(ethylene glycol) (PEG) on protein nanocages is a key parameter in determining their successful applications in vivo, including overcoming delivery route barriers such as mucus and still allowing for interactions between protein nanocages and targeted receptors on tumor cells. A dense coating of PEG on protein nanocages can allow rapid penetration through mucus because of the greatly reduced adhesive interaction between mucus constituents and nanoparticles.

Since protein nanocages are amenable to self-assembly, disassembly and reassembly at different environments (e.g., pH), units of protein molecules with different modifications can be mixed at user-selected ratios. For example, non-PEGylated ferritin molecules can be mixed with PEGylated ferritin molecules at ratios of 9:1, 8:2, 7:3, 6:4, 5:5, 4:6, 3:7, 2:8, 1:9, and 0:10, and the pH of the mixture adjusted to neutral or near neutral pH for the assembly of PEGylated ferritin nanocages at 10%, 20%, 30%, 40%, 50%, 60%, 70%, 80%, 90%, and 100% PEGylation proportions. Non-PEGylated ferritin nanocages and PEGylated ferritin nanocages can also be mixed at neutral or near neutral pH at designated ratios, and the pH of the mixture adjusted to acid pH (e.g., pH 2.0) for nanocage disassembly and protein unit mixing, then adjusted to neutral or near neutral (pH 7.4) for assembly of hybrid ferritin nanocages. Ferritin protein molecules with other functionalities such as covalently bound drugs, fluorescent dyes, and other tracking labeling can also be mixed with non-modified ferritin and/or PEGylated ferritin to form hybrid ferritin nanocages.

The density of PEG or other surface altering agents in protein nanocages depends on the number of bound PEG or other surface altering agents in each subunit of protein nanocages. For example, in the sequence of human ferritin heavy chain, 14 amino acids containing primary amines and three amino acids containing thiols are available for conjugation with PEG, dye, and/or drug. The density of PEG modified via amine-mediated bioconjugation techniques is higher than that modified via thiol-mediated bioconjugation techniques. For a high surface PEG density in ferritin nanocages, PEGylation via amine groups is generally preferred. Using thiol-maleimide chemistry to conjugate PEG to the surface of ferritin nanocages, a high surface density cannot be accomplished due to the limited amount of available thiol groups for PEG conjugation (Vannucci L, et al., *International Journal of Nanomedicine*, 7:1489-1509 (2012)).

Different methods can be used to assess the surface PEG density on nanoparticles.

Thermogravimetric analysis (TGA) can be used to calculate PEG content, but it is limited to inorganic materials and also requires the use of relatively large quantity of samples.

The reactions of dye and reagents (such as fluorescence dye) to functional PEG are widely used for PEG quantification. In these methods, the un-reacted PEG molecules with functional groups (such as —SH, —NH$_2$, etc.) are quantified by fluorescent assay or colorimetric quantification after the reaction with certain reagents, and the content of surface PEG calculated by subtracting the un-reacted PEG portion in supernatant. However, these methods are limited to surface PEGylation and functional PEG.

Quantitative $^1$H nuclear magnetic resonance (NMR) can be used to assess the surface PEG density on PEG-containing protein nanocages, both qualitatively and quantitatively (PEG proton peak, broad, typically observed ~3.65 ppm). When protein nanocages are dispersed within the NMR solvent $D_2O$, the surface PEG can be directly detected by NMR. By comparing with a calibration curve of PEG proton peak intensity over the concentration of PEG, the amount of surface PEG on protein nanocages is determined by NMR.

Fluorometric measurement or NMR provides a means for measuring PEG surface density, i.e., number of PEG molecules per unit surface area (#/nm$^2$). Dividing the quantity of PEG by the surface area of protein nanocages ([$4\pi(D/2)^2$] where D is the average diameter of protein nanocage) provides the number density of PEG (per area).

The density of the coating can be varied based on a variety of factors including the composition and molecular weight of the surface altering agent and the composition of the protein nanocages. In one embodiment, the density of the surface altering agent, such as PEG, as measured by $^1$H NMR is at least, 0.01, 0.02, 0.05, 0.08, 0.1, 0.2, 0.5, 0.8, 1, 2, 5, or 10 chains or molecules per nm$^2$, or 1, 2, 5, 8, 10, 15, 20, 40, 50, or 100 chains or molecules per 100 nm$^2$. The range above is inclusive of all values from 1 to 100 units per 100 nm$^2$.

In particular embodiments, the density of the surface altering agents, such as PEG, is from about 10 to about 70 chains/100 nm$^2$, from about 15 to about 50 chains/100 nm$^2$, from about 15 to about 45 chains/100 nm$^2$, from about 20 to about 45 chains/100 nm$^2$, from about 25 to about 45 chains/100 nm$^2$, or from about 35 to about 45 chains/100 nm$^2$. The concentration of the surface altering agent, such as PEG, can also be varied.

In some embodiments, the content of PEGylated protein subunits in the protein nanocages is at least 10%, 12.5%, 15%, 20%, 25%, 30%, 37.5%, 40%, 45%, 50%, 55%, 60%, 65%, 70%, 75%, 80%, 85%, 87.5%, 90%, 95%, or 100%. The range above is inclusive of all values from 10% to 100%. A threshold of generally 50% or more proportion of densely PEGylated ferritin in ferritin nanocages is needed for enhanced in vivo mucosal distribution and coverage, as well as colloidal stability.

In other embodiments, the mass of the surface-altering moiety is at least 1/10,000, 1/7500, 1/5000, 1/4000, 1/3400, 1/2500, 1/2000, 1/1500, 1/1000, 1/750, 1/500, 1/250, 1/200, 1/150, 1/100, 1/75, 1/50, 1/25, 1/20, 1/5, 1/2, or 9/10 of the mass of the protein nanocages. The range above is inclusive of all vales from 1/10,000 to 9/10.

In particular embodiments, the density of the surface-altering material (e.g., PEG) is such that the surface-altering material (e.g. PEG) adopts an extended/dense brush configuration, and the protein nanocages have a neutral or near neutral surface charge of between about −10 mV and about +10 mV.

To determine the conformation of PEG, the ratio [Γ/SA] of total unconstrained PEG surface area coverage [Γ] to total particle surface area [SA] indicates whether the PEG coating is in a mushroom or brush conformation, [Γ/SA]<1 or [Γ/SA]≥1, respectively (Boylan N J, et al., *J Control Release*, 157(1):72-79 (2012)). The total unconstrained PEG surface area coverage [Γ] is calculated by multiplying the area occupied at the surface per unconstrained PEG chain by the total number of PEG chains per protein nanostructure. The surface area occupied by an unconstrained PEG chain can be calculated by random-walk statistics and given by a sphere of diameter (ξ):

$$\xi = 0.76\, m^{1/2}\, [Å]$$

where m is the molecular weight of PEG chain.

A dense brush coating of PEG or other surface altering agents enhances the distribution and coverage of mucosal epithelium by protein nanocages and reduces the loss of protein nanocages trapped in mucus or cleared by mucus turnover, as compared to non-PEGylated or moderately coated protein nanocages, when delivered via a mucosal route. A dense brush coating also prevents aggregation of protein nanocages in physiological fluid or human plasma and improves the colloidal stability in physiologically relevant conditions, suitable for systemic delivery. Preferably, the protein nanocages even loaded with a therapeutic and/or diagnostic agent contains a mucus penetration enhancing material at a high surface density conferring brush-like coatings, e.g., [Γ/SA]≥1, and more preferably [Γ/SA]>2.

A dense brush coating or a high density of surface altering agents imparts enhanced mucus penetration to the nanocages. Selecting the molecular weights of surface altering agents ensures the capability of the protein nanocages to penetrate tumor tissues and mediate specific cellular uptake.

Low molecular weight PEG or other surface altering agents are generally preferred in effecting mucus penetration and maintaining the tumor targeting capability of ferritin nanocages. For example, 50% PEGylated ferritin nanocages with PEG 2 kDa are taken up more by TfR 1-expressing tumor cells than ones with PEG 5 kDa or 10 kDa. The preferred low molecular weights of surface altering agents depend on the density and composition of surface modification on protein nanocages, the characteristics of the proteins in forming the nanocages, and the routes of administration.

C. Therapeutic, Prophylactic and Diagnostic Agents

Agents for delivery can be physically entrapped in the protein nanocage cavity, encapsulated in the nanocages, non-covalently associates on the surface of the protein nanocage, and/or covalently bound to the proteins forming the nanocage.

Agents may also be physically incorporated, for example by trapping, internalization, or encapsulation to provide release of the additional agents with a different release rate, typically faster. Molecules in solution can be trapped within the cavity of ferritin nanocages by dis/assembling ferritin in the presence of drug solutions. This property can be used to load the cavity with metal containing drugs, such as platinum chemotherapeutics such as cisplatin and the iron chelator desferrioxamine B. Agents having a natural tendency to bind to metals are readily encapsulated by ferritin. Non-metal-containing drugs can be complexed with transition metals, such as Cu(II), prior to their internalization by ferritin nanocages, or the addition of charged accessory molecules such as poly-L-aspartic acid to optimize loading of ferritin with agents. Specific methods of these modifications of agents to be physically incorporated are known by those skilled in the art, for example, Maham A et al, *Small,* 5:1706-21 (2009) and *J Mater Chem,* 21:8700 (2011).

The percent agent loading is from about 1% to about 80%, from about 1% to about 50%, preferably from about 1% to about 40% by weight, more preferably from about 1% to about 20% by weight, most preferably from about 1% to about 10% by weight.

Therapeutic and Prophylactic Agents

Therapeutic and prophylactic agents can be proteins or peptides, sugars or polysaccharides, lipids, nucleic acids, or combinations thereof. In a preferred embodiment, these are small molecules, generally having a molecular weight of 2000 Daltons or less, more preferably 1000 Daltons or less. Exemplary classes of therapeutic agents include, but are not limited to, anti-proliferatives such as anti-cancer agents, anti-angiogenesis agents, analgesics, anti-inflammatory drugs, antipyretics, antiepileptics, antipsychotic agents, neuroprotective agents, anti-infectious agents, such as antibacterial, antiviral and antifungal agents, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, gastro-intestinal drugs, muscle relaxants, parasympathomimetics, stimulants, anorectics and anti-narcoleptics.

In some embodiments, the therapeutic agents linked or encapsulated in the protein nanocages are immune-modulating agents. For example, immune checkpoint inhibitors are covalently linked or encapsulated in ferritin nanocages. Checkpoint inhibitors include drugs, drug candidates, or agents that inhibit/block immune checkpoint molecules. There are generally two classes of immune checkpoint molecules, i.e., stimulatory checkpoint molecules and inhibitory checkpoint molecules. Stimulatory checkpoint molecules include CD27, CD28, CD40, CD122, CD137, OX40, glucocorticoid-Induced TNFR family Related gene (GITR), and inducible T-cell costimulator (ICOS). Inhibitory checkpoint molecules include adenosine A2A receptor (A2AR), B7-H3 (also called CD276), B7-H4, B and T Lymphocyte Attenuator (BTLA; also called CD272), cytotoxic T-Lymphocyte-Associated protein 4 (CTLA-4; also called CD152), indoleamine 2,3-dioxygenase (IDO), killer-cell immunoglobulin-like receptor (KIR), lymphocyte Activation Gene-3 (LAGS), programmed death 1 receptor (PD-1), T-cell immunoglobulin domain and mucin domain 3 (TIM-3), and V-domain Ig suppressor of T cell activation (VISTA) Immune checkpoint inhibitors may be antibodies that block immune checkpoint proteins on cancer cells or proteins on T cells, such that the protein blinders that prevented T cells from recognizing cancerous cells are removed, leading an immune system assault on cancerours cells. For example, PD-1 is a checkpoint protein on T cells. PD-L1 is another checkpoint protein found on many healthy cells in the body. When PD-1 binds to PD-L1, it stops T cells from killing a cell.

Exemplary checkpoint inhibitors for inclusion in protein nanocages with surface altering agents include ipilimumab (YERVOY®, a monoclonal antibody that attaches to CTLA-4 and stops it from working), pembrolizumab (KEYTRUDA®, a PD-1 inhibitor), nivolumab (OPDIVO®, a PD-1 inhibitor), atezolizumab (TECENTRIQ, a PD-L1 inhibitor), avelumab (BAVENCIO, a PD-L1 inhibitor), and durvalumab (IMFINZI, a PD-L1 inhibitor), each or in combination in an effective amount to a subject in need thereof.

Other anti-PD-1 antibodies are described in the following publications: PCT/IL03/00425 (Hardy et al., WO/2003/099196), PCT/JP2006/309606 (Korman et al., WO/2006/121168), PCT/US2008/008925 (Li et al., WO/2009/014708), PCT/JP03/08420 (Honjo et al., WO/2004/004771), PCT/JP04/00549 (Honjo et al., WO/2004/072286), PCT/IB2003/006304 (Collins et al., WO/2004/056875), PCT/US2007/088851 (Ahmed et al., WO/2008/083174), PCT/US2006/026046 (Korman et al., WO/2007/005874), PCT/US2008/084923 (Terrett et al., WO/2009/073533), Berger et al., Clin. Cancer Res., Vol. 14, pp. 30443051 (2008).

Exemplary anti-B7-H1 antibodies for inclusion in protein nanocages include, but are not limited to, those described in the following publications: PCT/US06/022423 (WO/2006/133396, pub. 14 Dec. 2006), PCT/US07/088851 (WO/2008/083174, pub. 10 Jul. 2008), and US 2006/0110383 (pub. 25 May 2006).

An immune modulating agent may also be a small molecule antagonist. Small molecules are generally small organic compounds having a molecular weight of less than about 2,500 Da. A series of small organic compounds have been shown to bind to the B7-1 ligand to prevent binding to CTLA4 (see Erbe et al., *J. Biol. Chem.*, Vol. 277, pp. 7363-7368 (2002). In other embodiments, anti-sense nucleic acids, both DNA and RNA, as well as siRNA molecules, target immune checkpoint molecules. For example, siRNA (for example, of about 21 nucleotides in length, which is specific for the gene encoding PD-1, or encoding a PD-1 ligand, and which oligonucleotides can be readily purchased commercially) complexed with carriers, such as polyethyleneimine (see Cubillos-Ruiz et al., J. Clin. Invest. 119(8): 2231-2244 (2009), are readily taken up by cells that express PD-1 as well as ligands of PD-1 and reduce expression of these receptors and ligands to achieve a decrease in inhibitory signal transduction in T cells, thereby activating T cells.

Preferred classes of small molecules to include in the protein nanocages include cancer therapeutics such as chemotherapeutic agents, cytokines, chemokines, and radiation therapy. The majority of chemotherapeutic drugs can be divided in to: alkylating agents, antimetabolites, anthracyclines, plant alkaloids, topoisomerase inhibitors, and other antitumor agents. All of these drugs affect cell division or DNA synthesis and function in some way. Additional therapeutics include monoclonal antibodies (including fragments thereof) and tyrosine kinase inhibitors e.g., imatinib mesylate (GLEEVEC® or GLIVEC®), which directly targets a molecular abnormality in certain types of cancer (chronic myelogenous leukemia, gastrointestinal stromal tumors).

In a preferred embodiment, the therapeutic agent is a chemotherapeutic, antitumor agent, e.g., a hypoxia-inducible factor 1-alpha (HIF-1α) inhibitor. Representative chemotherapeutic agents include, but are not limited to, doxorubicin, dexrazoxane, sorafenib, erlotinib hydrochloride, platinum containing drugs such as cisplatin, cetuximab, sunitinib, bevacizumab carboplatin, oxaliplatin, mechlorethamine, cyclophosphamide, chlorambucil, vincristine, vinblastine, vinorelbine, vindesine, taxol and derivatives thereof, irinotecan, topotecan, amsacrine, etoposide, etoposide phosphate, teniposide, epipodophyllotoxins, trastuzumab, rituximab and combinations thereof.

In some embodiments, the agent is one or more nucleic acids. The nucleic acid can alter, correct, or replace an endogenous nucleic acid sequence. The nucleic acid is used to treat cancers, correct defects in genes in other diseases and metabolic diseases affecting mucus-covered tissues, genes such as those for the treatment of Parkinsons and ALS where the genes reach the brain through nasal delivery. One example is MACUGEN® (pegaptanim sodium, anti-VEGF aptamer or EYEOO1) (Eyetech Pharmaceuticals).

Gene therapy is a technique for correcting defective genes responsible for disease development. There are several approaches for correcting faulty genes. A normal gene may be inserted into a nonspecific location within the genome to replace a nonfunctional gene. An abnormal gene could be swapped for a normal gene through homologous recombination. The abnormal gene could be repaired through selective reverse mutation, which returns the gene to its normal function. The regulation (the degree to which a gene is turned on or off) of a particular gene could be altered.

The nucleic acid can be a DNA, RNA, a chemically modified nucleic acid, or combinations thereof. For example, methods for increasing stability of nucleic acid half-life and resistance to enzymatic cleavage are known in the art, and can include one or more modifications or substitutions to the nucleobases, sugars, or linkages of the polynucleotide. The nucleic acid can be custom synthesized to contain properties that are tailored to fit a desired use. Common modifications include, but are not limited to use of locked nucleic acids (LNAs), unlocked nucleic acids (UNAs), morpholinos, peptide nucleic acids (PNA), phosphorothioate linkages, phosphonoacetate linkages, propyne analogs, 2'-O-methyl RNA, 5-Me-dC, 2'-5' linked phosphodiester linkage, Chimeric Linkages (Mixed phosphorothioate and phosphodiester linkages and modifications), conjugation with lipid and peptides, and combinations thereof.

In some embodiments, the nucleic acid includes internucleotide linkage modifications such as phosphate analogs having achiral and uncharged intersubunit linkages (e.g., Sterchak, E. P. et al., *Organic Chem.*, 52:4202, (1987)), or uncharged morpholino-based polymers having achiral intersubunit linkages (see, e.g., U.S. Pat. No. 5,034,506). Some internucleotide linkage analogs include morpholidate, acetal, and polyamide-linked heterocycles. Other backbone and linkage modifications include, but are not limited to, phosphorothioates, peptide nucleic acids, tricyclo-DNA, decoy oligonucleotide, ribozymes, spiegelmers (containing L nucleic acids, an apatamer with high binding affinity), or CpG oligomers.

Protein or peptide agents can be included in the protein nanocages, preferably on the surface where they do not interfere with the assembly of protein nanocages. The additional protein fragments or peptides can be physically incorporated, covalently bound, or recombinantly produced with the protein to form nanocages. They can be targeting ligands to further enhance the specificity of protein nanocages or therapeutic antibodies for functions such as anti-angiogenesis to treat cancer diseases.

Therapeutic protein, protein fragments, peptides or related compounds include antibodies to vascular endothelial growth factor (VEGF) such as bevacizumab (AVASTIN®) and rhuFAb V2 (ranibizumab, LUCENTIS®), and other anti-VEGF compounds; pigment epithelium derived factor(s) (PEDF); interferon alpha; interleukin-12 (IL-12); endostatin; angiostatin; ribozyme inhibitors such as ANGIOZYME® (Sirna Therapeutics); multifunctional anti-angiogenic agents such as NEOVASTAT® (AE-941) (Aeterna Laboratories, Quebec City, Canada; antibodies to the epidermal grown factor receptor such as panitumumab (VECTIBIX®) and cetuximab (ERBITUX®), as well as other anti-angiogenesis agents known in the art.

Other small molecules that can be delivered include COX-2 inhibitors such as celecoxib (CELEBREX®) and rofecoxib (VIOXX®); thalidomide (THALOMID®) and derivatives thereof such as lenalidomide (REVLIMID®); squalamine); receptor tyrosine kinase (RTK) inhibitors such as sunitinib (SUTENT®); tyrosine kinase inhibitors such as sorafenib (Nexavar®) and erlotinib (Tarceva®).

Exemplary diagnostic materials include paramagnetic molecules, fluorescent compounds, magnetic molecules, and radionuclides. Suitable diagnostic agents include, but are not limited to, x-ray imaging agents and contrast media. Radionuclides also can be used as imaging agents. Examples of other suitable contrast agents include gases or gas emitting compounds, which are radiopaque. Protein nanocages can further include agents useful for determining the location of administered nanocages. Agents useful for this purpose include fluorescent tags, radionuclides and contrast agents.

Linkers

Some embodiments provide degradable linkers in the covalent attachment of therapeutic, diagnostic, and imaging agents to the protein nanocages. These linkers can be sensitive to pH, enzymes, and/or external stimuli such as temperature and wavelength. For example, acid labile linkers allow intracellular release at endolysosomal vesicles of covalently attached therapeutic agents from the surface of protein nanocages. Tumor microenvironment can be slightly acidic (pH 6.5-6.8). In some embodiments, the protein nanocages delivers a therapeutic agent to be released only inside a tumor cell, where the therapeutic agent is covalently bonded with the protein nanocage via an acid-labile linker that requires substantially lower pH (<6.0) for degradation. For example, acid-labile linkers include hydrazones and cis-aconityl, e.g., cis-aconitic anhydride. A cis-aconityl linkage conjugates payloads, such as doxorubicin (DOX) and daunomycin (or daunorubicin), to carbohydrate hydroxyls groups of a protein or peptide. cis-Aconityl uses a carboxylic acid juxtaposed to an amide bond to accelerate amide hydrolysis under acidic conditions. Hydrazones utilize amino acid residues on a protein or peptide instead of the carbohydrate moieties for covalent attachment. These linkers retain intact and stable in a neutral pH environment (pH 7.3-7.5, e.g., during systemic circulation in the blood's) but undergo hydrolysis and release drug in an acidic environment (e.g., mildly acidic endosomal (pH 5.0-6.5) and lysosomal (pH 4.5-5.0) compartments). Further acid sensitive linkers are described in the U.S. Patent Application Publication No. 20110053878 A1. Stimuli labile linkers are described with stimuli-responsive nanocarriers in Ganta S, et al., *J Control Release*, 126:187-204 (2008).

Targeting Moieties

Ferritin nanocages are naturally selective for a number of different types of tumors. However, there may be embodiments where different or additional targeting is desired. Exemplary target molecules including proteins, peptides, nucleic acids, lipids, saccharides, or polysaccharides, or small molecules that bind to one or more targets associated with an organ, tissue, cell, or extracellular matrix, or specific type of tumor or infected cell, can be bound to the protein nanocages. The degree of specificity with which the protein nanocages target a substrate can be modulated through the selection of a targeting molecule with the appropriate affinity and specificity. For example, a targeting moiety can be a polypeptide, such as an antibody that specifically recognizes a tumor marker that is present exclusively or in higher amounts on a malignant cell (e.g., a tumor antigen). Suitable targeting molecules that can be used to direct nanoparticles to cells and tissues of interest, as well as methods of conjugating target molecules to nanoparticles, are known in the art. See, for example, Ruoslahti, et al. *Nat. Rev. Cancer*, 2:83-90 (2002). Targeting molecules can also include neuropilins and endothelial targeting molecules, integrins, selectins, and adhesion molecules.

Examples of targeting moieties include peptides such as iRGD, LyP1; small molecule such as folate, aptamers and antibodies or their combinations at various molar ratios.

The targeting elements should have an affinity for a cell-surface receptor or cell-surface antigen on the target cells and result in internalization of the particle within the target cell.

The targeting element can specifically recognize and bind to a target molecule specific for a cell type, a tissue type, or an organ. The target molecule can be a cell surface polypeptide, lipid, or glycolipid. The target molecule can be a receptor that is selectively expressed on a specific cell surface, a tissue or an organ. Cell specific markers can be for specific types of cells including, but not limited to stem cells, blood cells, immune cells, muscle cells, nerve cells, cancer cells, virally infected cells, and organ specific cells. The cell markers can be specific for endothelial, ectodermal, or mesenchymal cells. Representative cell specific markers include, but are not limited to cancer specific markers.

Additional targets that can be recognized by the targeting element include VEGF/KDR, Tie2, vascular cell adhesion molecule (VCAM), endoglin and $\alpha_5\beta_3$ integrin/vitronectin. The targeting peptides can be covalently associated with the polymer of the outer shell and the covalent association can be mediated by a linker.

In one embodiment the targeting element specifically binds to an antigen that is expressed by tumor cells. The antigen expressed by the tumor may be specific to the tumor, or may be expressed at a higher level on the tumor cells as compared to non-tumor cells. Antigenic markers such as serologically defined markers known as tumor associated antigens, which are either uniquely expressed by cancer cells or are present at markedly higher levels (e.g., elevated in a statistically significant manner) in subjects having a malignant condition relative to appropriate controls, are contemplated for use in certain embodiments.

Tumor-associated antigens may include, for example, cellular oncogene-encoded products or aberrantly expressed proto-oncogene-encoded products (e.g., products encoded by the neu, ras, trk, and kit genes), or mutated forms of growth factor receptor or receptor-like cell surface molecules (e.g., surface receptor encoded by the c-erb B gene). Other tumor-associated antigens include molecules that may be directly involved in transformation events, or molecules that may not be directly involved in oncogenic transformation events but are expressed by tumor cells (e.g., carcinoembryonic antigen, CA-125, melanoma associated antigens, etc.) (see, e.g., U.S. Pat. No. 6,699,475; Jager, et al., *Int. J. Cancer,* 106:817-20 (2003); Kennedy, et al., *Int. Rev. Immunol.,* 22:141-72 (2003); Scanlan, et al. *Cancer Immun.,* 4:1 (2004)).

Genes that encode cellular tumor associated antigens include cellular oncogenes and proto-oncogenes that are aberrantly expressed. In general, cellular oncogenes encode products that are directly relevant to the transformation of the cell, and because of this, these antigens are particularly preferred targets for immunotherapy. An example is the tumorigenic neu gene that encodes a cell surface molecule involved in oncogenic transformation. Other examples include the ras, kit, and trk genes. The products of proto-oncogenes (the normal genes which are mutated to form oncogenes) may be aberrantly expressed (e.g., overexpressed), and this aberrant expression can be related to cellular transformation. Thus, the product encoded by proto-oncogenes can be targeted. Some oncogenes encode growth factor receptor molecules or growth factor receptor-like molecules that are expressed on the tumor cell surface. An example is the cell surface receptor encoded by the c-erbB gene. Other tumor-associated antigens may or may not be directly involved in malignant transformation. These antigens, however, are expressed by certain tumor cells and may therefore provide effective targets. Some examples are carcinoembryonic antigen (CEA), CA 125 (associated with ovarian carcinoma), and melanoma specific antigens.

In ovarian and other carcinomas, for example, tumor associated antigens are detectable in samples of readily obtained biological fluids such as serum or mucosal secretions. One such marker is CA125, a carcinoma associated antigen that is also shed into the bloodstream, where it is detectable in serum (e.g., Bast, et al., *N. Eng. J. Med.,* 309:883 (1983); Lloyd, et al., *Int. J. Canc.,* 71:842 (1997). CA125 levels in serum and other biological fluids have been measured along with levels of other markers, for example, carcinoembryonic antigen (CEA), squamous cell carcinoma antigen (SCC), tissue polypeptide specific antigen (TPS), sialyl TN mucin (STN), and placental alkaline phosphatase (PLAP), in efforts to provide diagnostic and/or prognostic profiles of ovarian and other carcinomas (e.g., Sarandakou, et al., *Acta Oncol.,* 36:755 (1997); Sarandakou, et al., *Eur. J. Gynaecol. Oncol.,* 19:73 (1998); Meier, et al., *Anticancer Res.,* 17(4B):2945 (1997); Kudoh, et al., *Gynecol. Obstet. Invest.,* 47:52 (1999)). Elevated serum CA125 may also accompany neuroblastoma (e.g., Hirokawa, et al., *Surg. Today,* 28:349 (1998), while elevated CEA and SCC, among others, may accompany colorectal cancer (Gebauer, et al., *Anticancer Res.,* 17(4B):2939 (1997)).

The tumor associated antigen, mesothelin, defined by reactivity with monoclonal antibody K-1, is present on a majority of squamous cell carcinomas including epithelial ovarian, cervical, and esophageal tumors, and on mesotheliomas (Chang, et al., *Cancer Res.,* 52:181 (1992); Chang, et al., *Int. J. Cancer,* 50:373 (1992); Chang, et al., *Int. J. Cancer,* 51:548 (1992); Chang, et al., *Proc. Natl. Acad. Sci. USA,* 93:136 (1996); Chowdhury, et al., *Proc. Natl. Acad. Sci. USA,* 95:669 (1998)). Using MAb K-1, mesothelin is detectable only as a cell-associated tumor marker and has not been found in soluble form in serum from ovarian cancer patients, or in medium conditioned by OVCAR-3 cells (Chang, et al., *Int. J. Cancer,* 50:373 (1992)). Structurally related human mesothelin polypeptides, however, also include tumor-associated antigen polypeptides such as the distinct mesothelin related antigen (MRA) polypeptide, which is detectable as a naturally occurring soluble antigen in biological fluids from patients having malignancies (see WO 00/50900).

A tumor antigen may include a cell surface molecule. Tumor antigens of known structure and having a known or described function, include the following cell surface receptors: HER1 (GenBank Accession No. U48722), HER2 (Yoshino, et al., *J. Immunol.,* 152:2393 (1994); Disis, et al., Canc. Res., 54:16 (1994); GenBank Acc. Nos. X03363 and M17730), HER3 (GenBank Acc. Nos. U29339 and M34309), HER4 (Plowman, et al., *Nature,* 366:473 (1993); GenBank Acc. Nos. L07868 and T64105), epidermal growth factor receptor (EGFR) (GenBank Acc. Nos. U48722, and K03193), vascular endothelial cell growth factor (GenBank No. M32977), vascular endothelial cell growth factor receptor (GenBank Acc. Nos. AF022375, 1680143, U48801 and X62568), insulin-like growth factor-I (GenBank Acc. Nos. X00173, X56774, X56773, X06043, European Patent No. GB 2241703), insulin-like growth factor-II (GenBank Acc. Nos. X03562, X00910, M17863 and M17862), transferrin receptor (Trowbridge and Omary, *Proc. Nat. Acad. USA,* 78:3039 (1981); GenBank Acc. Nos. X01060 and M11507), estrogen receptor (GenBank Acc. Nos. M38651, X03635, X99101, U47678 and M12674), progesterone receptor (GenBank Acc. Nos. X51730, X69068 and M15716), follicle stimulating hormone receptor (FSH-R) (GenBank Acc. Nos. Z34260 and M65085), retinoic acid receptor (GenBank Acc. Nos. L12060, M60909, X77664, X57280, X07282 and X06538), MUC-1 (Barnes, et al., *Proc. Nat. Acad. Sci. USA,* 86:7159 (1989); GenBank Acc. Nos. M65132 and M64928) NY-ESO-1 (GenBank Acc. Nos. AJ003149 and U87459), NA 17-A (PCT Publication No. WO 96/40039), Melan-A/MART-1 (Kawakami, et al., *Proc. Nat. Acad. Sci. USA,* 91:3515 (1994); GenBank Acc. Nos. U06654 and U06452), tyrosinase (Topalian, et al., *Proc. Nat. Acad. Sci. USA,* 91:9461 (1994); GenBank Acc. No. M26729; Weber, et al., *J. Clin. Invest,* 102:1258 (1998)), Gp-100 (Kawakami, et al., Proc. Nat. Acad. Sci. USA, 91:3515 (1994); GenBank Acc. No. 573003, Adema, et al., J. Biol. Chem., 269:20126 (1994)); MAGE (van den Bruggen, et al., Science, 254:1643 (1991)); GenBank Acc. Nos. U93163, AF064589, U66083, D32077, D32076, D32075, U10694, U10693, U10691, U10690, U10689, U10688, U10687, U10686, U10685, L18877, U10340, U10339, L18920, U03735 and M77481), BAGE (GenBank Acc. No. U19180; U.S. Pat. Nos. 5,683,886 and 5,571,711), GAGE (GenBank Acc. Nos. AF055475, AF055474, AF055473, U19147, U19146, U19145, U19144, U19143 and U19142), any of the CTA class of receptors including in particular HOM-MEL-40 antigen encoded by the SSX2 gene (GenBank Acc. Nos. X86175, U90842, U90841 and X86174), carcinoembryonic antigen (CEA, Gold and Freedman, J. Exp. Med., 121:439 (1985); GenBank Acc. Nos. M59710, M59255 and M29540), and PyLT (GenBank Acc. Nos. J02289 and J02038); p 97 (melanotransferrin) (Brown, et al., J. Immunol., 127:539-46 (1981); Rose, et al., Proc. Natl. Acad. Sci. USA, 83:1261-61 (1986)).

Additional tumor associated antigens include prostate surface antigen (PSA) (U.S. Pat. Nos. 6,677,157; 6,673,545); β-human chorionic gonadotropin β-HCG) (McManus, et al., Cancer Res., 36:3476-81 (1976); Yoshimura, et al., Cancer, 73:2745-52 (1994); Yamaguchi, et al., Br. J. Cancer, 60:382-84 (1989): Alfthan, et al., Cancer Res., 52:4628-33 (1992)); glycosyltransferase β-1,4-N-acetylgalactosaminyltransferases (GalNAc) (Hoon, et al., Int. J. Cancer, 43:857-62 (1989); Ando, et al., Int. J. Cancer, 40:12-17 (1987); Tsuchida, et al., J. Natl. Cancer, 78:45-54 (1987); Tsuchida, et al., J. Natl. Cancer, 78:55-60 (1987)); NUC18 (Lehmann, et al., Proc. Natl. Acad. Sci. USA, 86:9891-95 (1989); Lehmann, et al., Cancer Res., 47:841-45 (1987)); melanoma antigen gp75 (Vijayasardahi, et al., J. Exp. Med., 171:1375-80 (1990); GenBank Accession No. X51455); human cytokeratin 8; high molecular weight melanoma antigen (Natali, et al., Cancer, 59:55-63 (1987); keratin 19 (Datta, et al., J. Clin. Oncol., 12:475-82 (1994)).

Tumor antigens of interest include antigens regarded in the art as "cancer/testis" (CT) antigens that are immunogenic in subjects having a malignant condition (Scanlan, et al., Cancer Immun., 4:1 (2004)). CT antigens include at least 19 different families of antigens that contain one or more members and that are capable of inducing an immune response, including but not limited to MAGEA (CT1); BAGE (CT2); MAGEB (CT3); GAGE (CT4); SSX (CT5); NY-ESO-1 (CT6); MAGEC (CT7); SYCP1 (CT8); SPANXB1 (CT11.2); NA88 (CT18); CTAGE (CT21); SPA17 (CT22); OY-TES-1 (CT23); CAGE (CT26); HOMTES-85 (CT28); HCA661 (CT30); NY-SAR-35 (CT38); FATE (CT43); and TPTE (CT44).

Additional tumor antigens that can be targeted, including a tumor-associated or tumor-specific antigen, include, but not limited to, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO0205, Mart2, Mum-1, 2, and 3, neo-PAP, myosin class I, OS-9, pml-RARα fusion protein, PTPRK, K-ras, N-ras, Triosephosphate isomeras, Bage-1, Gage 3,4,5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90 (Mac-2 binding protein\cyclophilin C-associated protein), TAAL6, TAG72, TLP, and TPS. Other tumor-associated and tumor-specific antigens are known to those of skill in the art and are suitable for targeting by the fusion proteins.

Antibody Targeting Elements

The targeting element can be an antibody or an antigen-binding fragment thereof. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. The antigen binding portion of the antibody can be any portion that has at least one antigen binding site, such as Fab, F(ab')$_2$, dsFv, sFv, diabodies, and triabodies. In certain embodiments, the antibody is a single chain antibody.

Aptamer Targeting Elements

Aptamers are oligonucleotide or peptide sequences with the capacity to recognize virtually any class of target molecules with high affinity and specificity. Aptamers bind to targets such as small organics, peptides, proteins, cells, and tissues. Unlike antibodies, some aptamers exhibit stereoselectivity. The aptamers can be designed to bind to specific targets expressed on cells, tissues or organs.

Pharmaceutical Compositions

The formulations contain an effective amount of mucus penetrating protein nanocages in a pharmaceutical carrier appropriate for administration to a mucosal surface or systemically. The formulations can be administered parenterally (e.g., by injection or infusion), topically (e.g., to the eye), intravaginally, or via pulmonary administration. The protein nanocages can be further encapsulated in mucus penetrating polymeric nano- or micro-particles for sustained release.

The protein nanocages can be further encapsulated or delivered in mucus penetrating polymeric particles. Mucus penetrating particles can rapidly penetrate mucus, retain at epithelial surface for long hours despite mucus turnovers, and contain a high loading of payloads such as protein nanocages. Thus, the protein nanocages can be released from these particles at epithelial surfaces in a sustained and controlled manner, and further penetrate tumor tissues to the hypoxic cores and deliver therapeutic agents within tumor cells.

Pulmonary Formulations

Pharmaceutical formulations and methods for the pulmonary administration of active agents to patients are known in the art.

The respiratory tract is the structure involved in the exchange of gases between the atmosphere and the blood stream. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung, where the exchange of gases occurs.

Formulations can be divided into dry powder formulations and liquid formulations. Both dry powder and liquid formulations can be used to form aerosol formulations. The term aerosol as used herein refers to any preparation of a fine mist of particles, which can be in solution or a suspension, whether or not it is produced using a propellant.

Liquid Formulations

Liquid formulations contain one or more protein nanocages suspended in a liquid pharmaceutical carrier.

Suitable liquid carriers include, but are not limited to, distilled water, de-ionized water, pure or ultrapure water, saline, and other physiologically acceptable aqueous solutions containing salts and/or buffers, such as phosphate buffered saline (PBS), Ringer's solution, and isotonic sodium chloride, or any other aqueous solution acceptable for administration to an animal or human.

Preferably, liquid formulations are isotonic relative to physiological fluids and of approximately the same pH, ranging from about pH 4.0 to about pH 7.4, more preferably from about pH 6.0 to pH 7.0. The liquid pharmaceutical carrier can include one or more physiologically compatible buffers, such as a phosphate buffers. One skilled in the art can readily determine a suitable saline content and pH for an aqueous solution for pulmonary administration.

Liquid formulations may include one or more suspending agents, such as cellulose derivatives, sodium alginate, polyvinylpyrrolidone, gum tragacanth, or lecithin. Liquid formulations may also include one or more preservatives, such as ethyl or n-propyl p-hydroxybenzoate.

Liquid formulations may also contain minor amounts of polymers, surfactants, or other excipients well known to those of the art. In this context, "minor amounts" means no excipients are present that might adversely affect uptake of the one or more active agents in the lungs.

Dry Powder Formulations

Dry powder formulations are finely divided solid formulations containing protein nanocages or the monomeric units which are suitable for pulmonary or nasal administration. Dry powder formulations include, at a minimum, one or more protein nanocages or self-assembling proteins or peptides which are suitable for pulmonary administration and the self-assembling proteins or peptides may self-assemble when resuspended in an aqueous medium. Such dry powder formulations can be administered via pulmonary inhalation to a patient without the benefit of any carrier, other than air or a suitable propellant.

The pharmaceutical carrier may include a bulking agent or a lipid or surfactant. Natural surfactants such as dipalmitoylphosphatidylcholine (DPPC) are the most preferred. Synthetic and animal derived pulmonary surfactants include Exosurf—a mixture of DPPC with hexadecanol and tyloxapol added as spreading agents, Pumactant (Artificial Lung Expanding Compound or ALEC)—a mixture of DPPC and PG, KL-4—composed of DPPC, palmitoyl-oleoyl phosphatidylglycerol, and palmitic acid, combined with a 21 amino acid synthetic peptide that mimics the structural characteristics of SP-B. Venticute—DPPC, PG, palmitic acid and recombinant SP-C. Animal derived surfactants include Alveofact—extracted from cow lung lavage fluid, Curosurf—extracted from material derived from minced pig lung, Infasurf—extracted from calf lung lavage fluid, Survanta—extracted from minced cow lung with additional DPPC, palmitic acid and tripalmitin.

The pharmaceutical carrier may also include one or more stabilizing agents or dispersing agents. The pharmaceutical carrier may also include one or more pH adjusters or buffers. Suitable buffers include organic salts prepared from organic acids and bases, such as sodium citrate or sodium ascorbate. The pharmaceutical carrier may also include one or more salts, such as sodium chloride or potassium chloride.

Dry powder formulations are typically prepared by blending one or more protein nanocages or the self-assembling proteins or peptides with one or more pharmaceutically acceptable carriers. Optionally, additional active agents may be incorporated into the mixture as discussed below. The mixture is then formed into particles suitable for pulmonary administration using techniques known in the art, such as lyophilization, spray drying, agglomeration, spray coating, coacervation, low temperature casting, milling (e.g., air-attrition milling (jet milling), ball milling), high pressure homogenization, and/or supercritical fluid crystallization.

Dry powder formulations can be administered as dry powder using suitable methods known in the art. Alternatively, the dry powder formulations can be suspended in the liquid formulations, and administered to the lung using methods known in the art for the delivery of liquid formulations.

The dry powder and liquid formulations described above can be used to form aerosol formulations for pulmonary administration. Aerosols for the delivery of therapeutic agents to the respiratory tract are known in the art. The term aerosol as used herein refers to any preparation of a fine mist of solid or liquid particles suspended in a gas. In some cases, the gas may be a propellant; however, this is not required. Aerosols may be produced using a number of standard techniques, including as ultrasonication or high pressure treatment.

In some cases, a device is used to administer the formulations to the lungs. Suitable devices include, but are not limited to, dry powder inhalers, pressurized metered dose inhalers, nebulizers, and electrohydrodynamic aerosol devices. Inhalation can occur through the nose and/or the mouth of the patient. Administration can occur by self-administration of the formulation while inhaling or by administration of the formulation via a respirator to a patient on a respirator.

Injectable Formulations

In some embodiments, the protein nanocages are formulated for parenteral delivery, such as injection or infusion, in the form of a solution or suspension. The formulation can be administered via any route, such as, the blood stream or directly to the organ or tissue to be treated. For example, parenteral administration may include administration to a patient intravenously, intradermally, intraperitoneally, intrapleurally, intratracheally, intramuscularly, subcutaneously, subjunctivally, by injection, and by infusion.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-laurylβ-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 4-8, more preferably around 5.5-7.5 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

In still other embodiments, the protein nanocages are formulated for topical administration to mucosa. Suitable dosage forms for topical administration include creams, ointments, salves, sprays, gels, lotions, emulsions, liquids, and transdermal patches. The formulation may be formulated for transmucosal, transepithelial, transendothelial, or transdermal administration. The compositions contain one or more chemical penetration enhancers, membrane permeability agents, membrane transport agents, emollients, surfactants, stabilizers, and combination thereof.

In some embodiments, the protein nanocages can be administered as a liquid formulation, such as a solution or suspension, a semi-solid formulation, such as a lotion or ointment, or a solid formulation. In some embodiments, they are formulated as liquids, including solutions and suspensions, such as eye drops or as a semi-solid formulation, such as ointment or lotion for topical application to mucosa, such as the eye or vaginally or rectally.

Suitable classes of penetration enhancers are known in the art and include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols).

Buffers are used to control pH of a composition. Preferably, the buffers buffer the composition from a pH of about 4 to a pH of about 7.5, more preferably from a pH of about 6 to a pH of about 7.5, and most preferably from a pH of about 6.5 to a pH of about 7.4. In a preferred embodiment, the buffer is phosphate buffered saline.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art. These preferably are enteric coated to avoid disassembly when passing through the stomach Formulations may be prepared using one or more pharmaceutically acceptable excipients, including diluents, preservatives, binders, lubricants, disintegrators, swelling agents, fillers, stabilizers, and combinations thereof.

Excipients, including plasticizers, pigments, colorants, stabilizing agents, and glidants, may also be used to form coated compositions for enteral administration. Formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment and process for preparing tablets and capsules and delayed release dosage forms of tablets, capsules, and granules.

III. Methods of Making Protein Nanocages

A. Protein Expression or Peptide Synthesis

Proteins, protein fragments, or polypeptides can be obtained by isolation from a natural source or, preferably, recombinant production. The nucleic acid encoding the proteins with intrinsic tumor targeting capability or recombinantly designed to include contain targeting specificity can be used to transform, transduce, or transfect a bacterial or eukaryotic host cell (e.g., an insect, yeast, or mammalian cell). Useful prokaryotic and eukaryotic systems for expressing and producing polypeptides are well known in the art.

Alternatively, some polypeptides are synthesized in a solid phase peptide synthesis process. Solid phase peptide synthesis is a known process in which amino acid residues are added to peptides that have been immobilized on a solid support.

B. Assembly of Protein Nanocages

FIG. 1A is a schematic of FTn disassembly at low pH and reassembly at neutral pH. The method forms mucus penetrating protein nanocages using self-assembly, disassembly and reassembly at different environments (e.g., pH and concentration of urea). Protein molecules with different modifications (e.g., associated with surface altering agents, associated with therapeutic agents, or labeled with imaging agents) can be mixed at user-selected ratios. A plurality of self-assembling proteins or their assembled nanocages, at least 30%, 40%, or 50% of the plurality containing mucus penetration enhancing materials, are mixed in a solution; the pH adjusted to strong acidity (e.g., pH 2) or basicity, and/or urea added to dissemble the protein nanocages; and the pH and/or urea adjusted protein solution adjusted to neutral or near neutral pH and/or the urea removed to form mucus penetrating protein nanocages. Example 1 below demonstrates assembly of the protein nanocages.

In preferred embodiments, surface altering agents are covalently bound to units of protein molecules that are assembled to form protein nanocages. For example, in the sequence of human ferritin heavy chain, 14 amino acids containing primary amines and three amino acids containing thiols are available for conjugation with PEG, dye, and/or drug. The density of PEG modified via amine-mediated bioconjugation techniques is higher than that modified via thiol-mediated bioconjugation techniques, in each human native heavy chain ferritin protein and associated ferritin nanocages. For a high surface PEG density in ferritin nanocages, PEGylation via amine groups is generally preferred.

Since protein nanocages are amenable to self-assembly, disassembly and reassembly in different environments (e.g., pH), units of protein molecules with different functionalities can be mixed at user-selected ratios. For example, non-PEGylated ferritin molecules can be mixed with PEGylated ferritin molecules at 9:1, 8:2, 7:3, 6:4, 5:5, 4:6, 3:7, 2:8, 1:9, and 0:10 molar ratios, and the pH of the mixture is tuned to neutral or near neutral pH for the assembly of PEGylated ferritin nanocages at 10%, 20%, 30%, 40%, 50%, 60%, 70%, 80%, 90%, and 100% PEGylation proportions. Non-PEGylated ferritin nanocages and PEGylated ferritin nanocages can also be mixed at neutral or near neutral pH at designated ratios, and the pH of the mixture is tuned to acidity (e.g., pH 2.0) for nanocage disassembly and protein unit mixing and further tuned to neutral or near neutral (pH 7.4) for assembly of hybrid ferritin nanocages. Ferritin protein molecules with other functionalities such as covalently bound drugs, fluorescent dyes, and other tracking labeling can also be mixed with non-modified ferritin and/or PEGylated ferritin to form hybrid ferritin nanocages.

IV. Methods of Using Protein Nanocages

The surface-altered protein nanocages can enhance delivery of active agents throughout tumor tissue. Surface altering agents generally create a neutral or near neutral surface charge (e.g., between about −10 mV and about +10 mV) for protein nanocages, which can enhance transport through bodily fluids and materials in vivo, including human mucus barriers, uniformly distribute at mucosal tissue, and are stable in circulation, whereas non-coated protein nanocages are immobilized in mucus or aggregated in plasma.

Most chemotherapy approaches for the treatment of lung airway cancers fail due to an inability to provide a sufficient drug dose to the entire tumor without life-threatening toxicity. The mucus penetrating protein nanocages can rapidly penetrate and uniformly distribute at different mucosal surfaces (preferentially partitioning at tumor sites), such as eyes, nose, lungs, gastrointestinal tract, vagina, and more, and therefore reduce the dosage required if active agents are delivered in mucus-immobilized protein nanocages. These protein nanocages can deliver active agents at a high local concentration and lower the total dose because of its deep penetration in tumor tissue past mucus barrier and selective targeting tumor tissue versus healthy tissue. The chemical composition, molecular weight, and density of the surface altering agents do not hinder the tumor targeting interactions between protein nanocages and cancer cells. Therefore, deep penetration within tumor tissue including the hypoxic core and intracellular delivery of active agents can be realized.

The mucus penetrating protein nanocages can also be used for screening candidate agents in tumor tissues, because the protein nanocages not only penetrate deep in tumor tissues but are also effectively uptaken by tumor cells.

The protein nanocages maintain the capability to be uptaken up by tumor cells and are able to release drug payloads only within certain cellular compartments, enabling deep penetration and specific payload release at tumor tissue and within tumor cells.

In some embodiments, the coated protein nanocage with a therapeutic, prophylactic, and/or diagnostic agent is used as a stand-alone therapy for patients with tumors. In other embodiments, the coated nanocage with a therapeutic, prophylactic, and/or diagnostic agent is used as an adjuvant therapy combined with systemic chemo- or immunotherapy.

Although the surface altering agents as a coating on the surface of protein nanocages provides mucus penetration capability suitable for administration at a mucosal surface, the coated protein nanocages are also suitable for systemic delivery via routes such as intravenous administration.

The present invention will be further understood by reference to the following non-limiting examples.

Example 1. PEGylation of Ferritin Nanocage (FTn) and Assembly of Hybrid FTn

Materials and Methods

Recombinant Human Ferritin Heavy Chain

A plasmid encoding human ferritin heavy chain was constructed by typical molecular cloning. Briefly, human cDNA was extracted from HCT116 human colon carcinoma cells. The gene encoding the human ferritin heavy chain was amplified by polymerase chain reaction (PCR) using a forward primer (5'-CGCCATATGACGACCGCGTC-CACCTCG-3', SEQ ID: 3) and a reverse primer (5'-CCGCTCGAGTTAGCTTTCATTAT-CACTGTCTCCCAGGGT-3', SEQ ID: 4). The PCR product was subsequently cloned into pET-21a (+) plasmid using NdeI and XhoI as restriction sites and the resulting plasmid vector was transformed into E. coli BL 21. A 1 L culture of E. coli transformed with pET-21a (+) ferritin heavy chain plasmid was grown to an $OD_{600}$ of ~0.8 in LB medium containing 100 μg/mL ampicillin. The protein production was induced by 1 mM IPTG for 4 hours, and subsequently, the cells were collected by centrifugation. After sonication, the cell lysate in Tris-Cl buffer (20 mM, pH 7.4) was centrifuged to remove E. coli debris. The supernatant was heated at 60° C. for 10 minutes to precipitate endogenous E. coli proteins. The resultant supernatant was then subjected to gel-filtration chromatography (GFC) with a Superose 6 column (GE Healthcare) to yield purified FTn protein. The purified FTn was confirmed by western blot assay using anti-ferritin heavy chain Ab (Abcam).

The sequence of human ferritin heavy chain is shown in SEQ ID:2.

Characterizations of FTn

The cage-like nanostructure of FTn at neutral pH was characterized by Hitachi H7600 transmission electron microscopy (TEM) after negative staining with 1% uranyl acetate. FTn concentration was determined by Bio-Rad protein assay kit (Bio-Rad Laboratories, Inc.).

PEGylation or Conjugation with Fluorescent Dyes on the Surface of FTn

To densely conjugate PEG on the surface of FTn, the nanocages were covalently modified with (MeO)-PEG-succinimidyl ester (molecular size, 2, 5, and 10 kD; Creative PEGWorks) by NHS-amine reaction. Briefly, 500 molar equivalents of mPEG-NHS with different MWs were added to the FTn solution (PBS, pH 7.4). The solution was placed on a rotary incubator for 4 hours and then concentrated by centrifugation (Amicon Ultra-0.5 mL 30 K MWCO; Millipore). The PEGylated FTn was purified and collected by a PD-10 desalting column (GE Healthcare). To determine the number of surface PEG per nanocage, FITC-PEG-NHS (Ex 485 nm, Em 528 nm, MW 2000; NANOCS) was identically conjugated to FTn. The density was fluorometrically determined (Suk J S, et al., Advanced Drug Delivery Reviews, 99(Pt A):28-51, Epub 2015). For the fluorescent labeling for other studies, 100 molar equivalents of dyes, either Cy 5 (Ex 650 nm, Em 670 nm; GE Healthcare) or AF488 (Ex 490 nm, Em 525 nm; Life technologies), were reacted with FTn and subsequently purified using a PD-10 desalting column.

Reassembly and Characterization of Hybrid FTn

Different FTn types, including non-PEGylated FTn, fluorescently labeled FTn (either AF488- or Cy5-labeled FTn) and FTn-$PEG_x$ (x=2, 5 or 10 kDa), were disassembled at pH=2 and reassembled at various blending ratios to yield hybrid FTn. Typically, different FTn types were mixed at designated molar ratios in PBS (pH 7.4) at a final protein concentration of 0.4 μM and were disassembled to subunits by adjusting pH to 2. Following a 20-minute incubation, pH was tuned back to 7.0-7.4. The mixture was incubated overnight for the reassembly of nanocages to lead to hybrid FTn. Based on an optimization process, PEGylated FTn (i.e. FTn/FTn-$PEG_x$) were formulated with 50% of FTn-$PEG_x$ in all studies. For the fluorescently labeling of PEGyalted FTn, half of the non-PEGylated FTn were replaced with fluorescently labeled FTn (i.e. 25 mol % FTn, 25 mol % fluorescently labeled FTn, and 50 mol % pegylated FTn).

Characterizations of Hybrid FTn

Hydrodynamic diameters (HD) of FTn and disassembled FTn were analyzed by GFC equipped with a Superose 6 column following previous reports (Choi H S, et al., Nature Nanotechnology, 5, 42-47(2010); Huang X, et al., ACS Nano, 7, 5684-5693 (2013)). Briefly, the protein standards with known HD (Bio-Rad), including M1 (thyroglobulin; 669 kDa, 18.8 nm HD), M2 (γ-globulin; 158 kDa, 11.9 nm HD), M3 (ovalbumin; 44 kDa, 6.13 nm HD), M4 (myoglobin; 17 kDa, 3.83 nm HD) and M5 (vitamin B12; 1.35 kDa, 1.48 nm HD), were analyzed using GFC and subsequently a standard curve of HD vs retention time was established.

The hybrid FTn was also characterized by gel electrophoresis. To enable the detection of signal from the gel by UV light excitation, AF488-labeled hybrid FTn were used for this study. The labeled FTn were analyzed following electrophoresis in a 0.5 agarose gel by electrophoresis.

To assess the PEG surface density on PEG-FTn, hybrid nanocages were formulated with FTn and FITC-labeled FTn-$PEG_{2k}$. The number of PEG chains per PEG-FTn was fluorometrically determined.

Results

Recombinant FTn was made by transforming bacterial cells with a custom-made plasmid encoding for human native ferritin heavy chain.

Figure 1B:
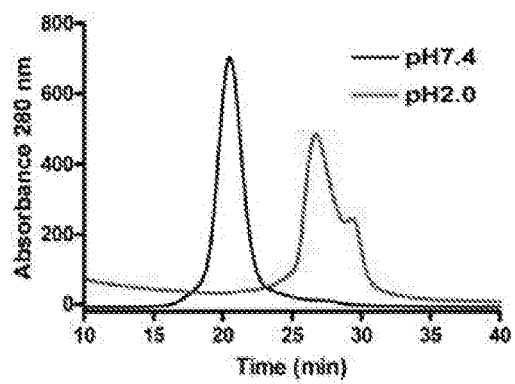
Figure 1C:
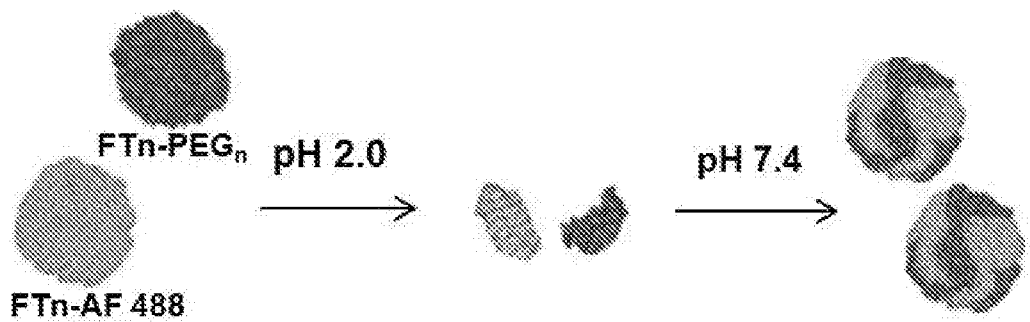

Subsequently, purified FTn were confirmed to undergo controlled cage dissociation under acidic conditions and reassembly at neutral pH. Transmission electron microscopy (TEM) revealed that FTn existed as monodispersed nanocages at pH 7.4, whereas FTn dissociated to individual subunits at pH 2, which were reassembled to form nanocages when the pH was returned to 7.4 (FIG. 1A). Size exclusion chromatography analysis showed FTn at pH 7.4 eluted out earlier than FTn at pH 2 (FIG. 1B). The diameters of FTn at pH 7.4 and at pH 2 were calculated from the standard curve of retention times for protein standards of known sizes (FIG. 1C), yielding a single peak at the size of 13.2 nm at pH 7.4 and a broad peak with a size range of 1.8-5.4 nm at pH 2.0.

PEG was conjugated to the primary amines exposed on the outer surface of FTn at neutral pH. Each ferritin heavy chain had 14 primary amines based on sequence analysis, and 24 chains of ferritin self-assembled into a nanocage. In each FTn, 336 primary amines are present. The surface density of 2 kDa PEG ($PEG_{2k}$) conjugated at a reaction molar ratio of 500:1 (PEG:FTn) was fluorometrically determined to be ~0.4 PEG/$nm^2$, which corresponds to ~190 PEG per FTn. Likewise, 5 and 10 kDa PEG ($PEG_{5k}$ and $PEG_{10k}$, respectively) were conjugated to separate aliquots of FTn. All PEGylated FTn (denoted FTn-$PEG_n$, where n=molecular weight of PEG, e.g., the conjugation with 2 kDa PEG was denoted as FTn-$PEG_{2k}$) exhibited cage-like structures that appeared similar to FTn prior to PEGylation under TEM. PEGylation does not affect reassembly of FTn.

The surface density of the fluorescent dye, Cy 5, conjugated at a reaction ratio of 100:1 (Cy5:FTn) was ~23 dye molecules per FTn. The surface density of another fluorescent dye, AF488, conjugated at a reaction ratio of 100:1 (AF488:FTn) (denoted FTn-AF488) was ~32 per FTn.

Figure 1D:
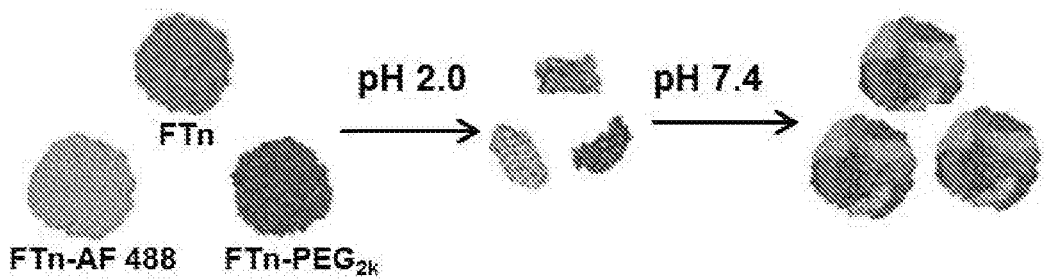

After FTn dissembled and different types of FTn reassembled. For example, FTn-AF488 and FTn-PEGx were dissembled at pH 2.0 into subunits, which reassembled into hybrid nanocages at pH 7.4 (FIG. 1D). FTn-AF488, FTn, and FTn-PEGx were dissembled at pH 2.0 into subunits, which reassembled at pH 7.4 into hybrid nanocages containing subunits from each of the three types of nanocages (FIG. 1E). TEM analysis confirmed the blending process did not disrupt the formation of cage-like hybrid FTn. Gel electrophoresis confirmed increasing the fraction of PEGylated FTn or increasing the MW of PEG used in creating hybrid FTn decreased the running rates on the gels, which provided evidence that the overall MW of PEGylated FTn increased.

In order to minimally affect the intrinsic targeting ability of FTn, subsequent studies were conducted with hybrid FTn containing a 1:1 molar ratio of FTn and FTn-PEG$_x$ (FTn/FTn-PEG$_x$), unless otherwise stated, because they exhibited minimal to no detrimental effect on the targeting ability toward tumor cells compared to pure FTn without PEG conjugation. Theoretically, inclusion of 50 mol % peyglated FTn should result in the surface PEG density of ~0.2 PEG/nm$^2$, a PEG density that was expected to lead to a brush-like conformation of PEG (Xu Q, et al., *ACS Nano*, 9, 9217-9227 (2015)). Fluorometric measurement determined that the PEG surface density was ~0.24±0.03 PEG/nm$^2$ for a hybrid nanocage containing 50 mol % FTn and 50 mol % FTn-PEG$_{2k}$. This was calculated with the following formula where D is the average diameter of PEG-FTn:

$$[\Gamma] = \text{PEG molecules} \div [4\pi(D/2)^2].$$

The ratio [Γ/SA] of total unconstrained PEG surface coverage area [Γ] to total particle surface area [SA] determines the surface PEG conformation: low-density mushroom and high-density brush regimes when [Γ/SA]<1 and [Γ/SA]≥1, respectively (Xu Q, et al., *ACS Nano*, 9. 9217-9227 (2015); Auguste D T, *Biomaterials*, 27, 2599-2608 (2006)). Briefly, the surface area occupied by one unconstrained PEG chain was calculated by random-walk statistics and given by a sphere of diameter ξ:

$$\xi = 0.76 \, m^{1/2} [\text{Å}],$$

where m is MW of PEG chain, and the surface area occupied by one PEG molecule can be determined by $\pi(\xi/2)^2$. Thus, the surface area occupied by unconstrained PEG of MWs 10, 5 and 2 kDa is 45, 23 and 9 nm$^2$, respectively. The total unconstrained PEG surface area coverage [Γ] was then calculated by multiplying the area occupied at the surface per PEG chain by the total number of PEG chains per protein nanocage. Thus, the [Γ/SA] ratio is 2.2±0.3, which falls in the dense brush regime.

Example 2. Effects of PEGylation Density on Colloidal Stability, Tumor Cell Uptake, and Tumor Tissue Penetration Materials and Methods Polyethylene glycol (PEG; 2 kDa) polymers were conjugated to human native heavy chain ferritin nanocages (FTn) at 0.42 PEG/nm$^2$ via an NHS-amine reaction, as described in Example 1. Non-PEGylated and PEGylated FTn were then disassembled at pH=2, followed by reassembly at pH=7 at 0, 25, 37.5, 50, 75, or 87.5% of PEGylated ferritin protein.

Nanocages reassembled in phosphate buffered saline (PBS) with varying % of PEGylated protein were analyzed by electrophoresis within a 0.5% agarose gel to determine any aggregation. For testing stability of FTn in human plasma, reassembled FTn products were incubated with 10% human plasma for 1 hour at 37° C. prior to electrophoresis.

The effects of PEG surface density on tumor cell uptake and tumor tissue penetration of FTn were studied using 3LL cell culture and three-dimensional (3D) tumor spheroid, respectively. See detailed procedures as described in Example 4. For microscopic visualization and quantification, a fluorescence dye, Cy5, was conjugated to FTn.

The primary goal of this study was to identify an optimal PEG density that provided desired benefit of PEG (i.e. colloidal stability, resistance to non-specific adhesive interactions, etc.), while retaining the intrinsic ability of FTn to target tumors cells via transferrin receptor (TfR-1).

Results

A higher mol % of PEGylated ferritin in the mixture with non-pegylated ferritin led to a greater PEG surface density in the reassembled nanocage formed with non-PEGylated and PEGylated FTn.

TABLE 1

PEGylated ferritin (%) and PEG surface density of reassembled FTn.

| % PEGylated protein | 0 | 25 | 37.5 | 50 | 75 | 87.5 |
|---|---|---|---|---|---|---|
| PEG$_{2k}$ density (#/nm$^2$) | 0 | 0.11 | 0.16 | 0.21 | 0.32 | 0.37 |

Non-PEGylated FTn aggregated and were stuck in the wells during electrophoresis, as well as moderately PEGylated FTn. In contrast, densely PEGylated FTn, formulated with ≥75% PEGylated ferritin protein (i.e. ≤25% non-PEGylated ferritin protein), resisted aggregation and efficiently migrated through the gel. These findings indicated dense PEGylation provided enhanced colloidal stability of FTn in physiologically relevant conditions.

A high surface PEG density was accomplished due to the abundance of primary amines on each ferritin. As detailed in Example 1, fourteen amine groups were available on each ferritin for NHS-amine mediated conjugation with PEG. This was different from previous art utilizing thiol-maleimide chemistry for conjugation of PEG on ferritin, because there were only three thiol groups in each human native heavy chain ferritin protein.

Figure 2A:
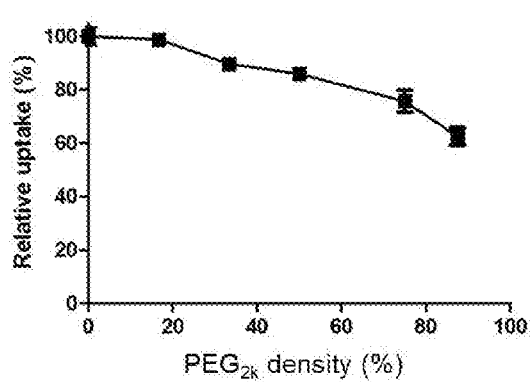

FIG. 2A shows increasing the PEG density slightly reduced uptake of FTn by 3LL cells. Densely PEGylated FTn formulated with 50% PEGylated ferritin protein retained more than 80% of tumor cell uptake compared to non-PEGylated FTn. Densely PEGylated FTn formulated with 75% PEGylated ferritin protein retained approximately 80% of tumor cell uptake compared to non-PEGylated FTn.

Figure 2B:
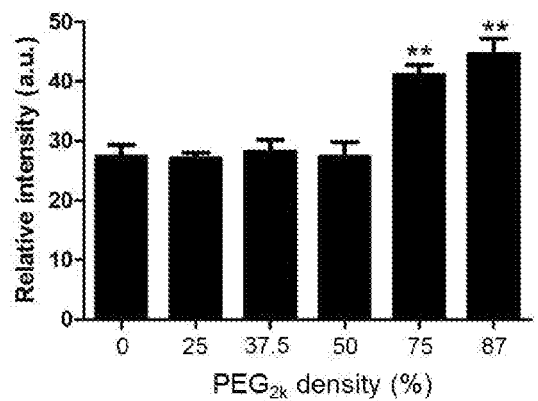

Fluorescent microscopy imaging of sections of 3D tumor spheroids showed FTn with moderately and densely coated PEG penetrated deep within the tumor spheroids. FIG. 2B shows the overall amount of protein nanocages within the tumor spheroids (i.e. 3D tumor penetration), as indicated by the intensity of fluorescence dye labeling FTn, was significantly greater for densely (e.g. ≥75%) PEGylated FTn compared to FTn with no or moderate PEGylation.

Example 3. In Vivo Airway Distribution of PEGylated FTn

Materials and Methods

The airway distribution of Cy5-labeled FTn, with or without PEG surface coatings, was studied following intranasal administration in mice. All experiments were approved by the Institutional Animal Care and Use Committee.

Female CF-1 mice (6-8 week) were anesthetized under continuous flow of isoflurane (2% in oxygen). A 50 μL solution of Cy 5-labeled FTn (5 μM) without or with PEG modification was each administered to the lung of different mice via intranasal instillation. The administered included one of the four groups: (1) Cy 5-labeled FTn, (2) Cy 5-labeled FTn/FTn-PEG$_{2k}$ (PEG MW=2 kDa), (3) Cy 5-labeled FTn/FTn-PEG$_{5k}$, and (4) Cy 5-labeled FTn/FTn-PEG$_{10k}$. Ten minutes after administration, mice were sacrificed and the entire lungs (including trachea) were removed and frozen in Tissue-Tek optimal cutting temperature compound (Sakura Finetek). Tracheas were sectioned on a Leica Cryostat (Leica Biosystems) with a section thickness of 10 µm. The sections were stained with Prolong Gold antifade with DAPI (Life technologies), and fluorescence images of the sections were obtained using a Zeiss confocal microscope. To quantify the particle distribution, the acquired images were analyzed by following an image-based analysis method that was previously reported (Mastorakos P, et al., *Proc Nat Acad Sci USA*, 112(28):8720-5 (2015)). Briefly, at least 10 fluorescence images at 10× magnification were taken for the lungs harvested from individual animals. The images were quantified with ImageJ software. An average coverage and total particles in airways were determined for each mouse, and then these values were averaged over a group of n=4 mice.

Results

Figure 2C:
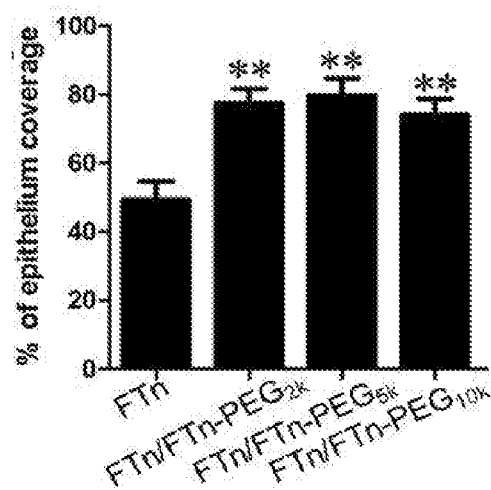
Figure 2D:
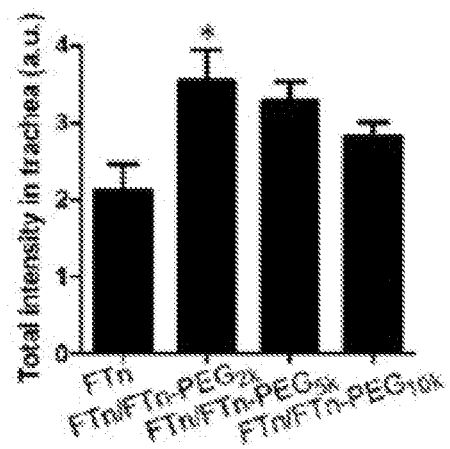

Non-PEGylated FTn aggregated in the mucus gel layer and, thus, were sparsely distributed in airways. In contrast, PEGylated FTn, regardless of PEG MW of 2, 5, or 10 kDa, exhibited uniform and widespread distribution throughout the mucus-covered large airways (i.e., trachea) in the mouse lung. The air-liquid interface layer of mouse appears to be around 50 µm in thickness. Quantitatively, FTn/FTn-PEG$_{2k}$, FTn/FTn-PEG$_{5k}$ and FTn/FTn-PEG$_{10k}$ covered 77±8%, 80±8% and 74±8% of the mouse tracheal surfaces, respectively, compared to only 50±9% by non-PEGylated FTn (p<0.01) (FIG. 2C). FTn/FTn-PEG$_{2k}$ and FTn/FTn-PEG$_{5k}$ were retained at higher levels in the lung airways compared to non-PEGylated FTn, as determined by quantifying the overall fluorescence intensity (FIG. 2D). This was in agreement with previous observation with polymer-based DNA nanoparticles (Suk J S, et al., *J Control Release*, 178:8-17 (2014)).

Example 4. Low MW PEGylation Did not Interfere with the Cancer Cell Targeting Capacity of FTn or its Penetration in Tumor Spheroids Materials and Methods
Intracellular Trafficking of FTn Mouse Lewis lung carcinoma (3LL) cells were incubated with different concentrations (0, 5, 10, 20, 40, or 80 nM) of Cy 5-labeled FTn for 2 hours. Subsequently, cells were incubated with Vibrant® DiO cell labeling solution (Life technologies) for 10 minutes following manufacturer's protocol (sub-cellular localization at cell membranes & lipids). After three times washing with PBS, the cells were fixed with Z-fix solution (Anatech) for 15 min, followed by 1.5 µg/mL DAPI staining at room temperature. The images of cells were acquired with a Zeiss LSM 510 Meta confocal microscope (Carl Zeiss) to study the uptake of FTn by 3LL cells.

Receptor-Mediated Cell Uptake of FTn Formulations

The specific interaction of varying FTn formulations and cell surface transferrin receptor 1 (TfR 1) was assessed by flow cytometry. Briefly, a 100 µL cell suspension (1×10$^6$ cells/mL) was incubated with 2 nM of Cy5-labeled FTn or hybrid FTn, including PEG-FTn, with or without 10-fold molar excess of anti-TfR 1 Ab for 30 minutes at 4° C. After washing with cold PBS, cells were analyzed using an AccuriC6 flow cytometer (BD Biosciences). In addition, the binding of Cy5-labeled FTn in the presence of increasing amounts (range: 0-8 µM) of non-PEGylated FTn or 50% PEGylated FTn was assay to study any competitive effects. The data was fitted to a binding curve via non-linear regression method using GraphPad Prism (GraphPad Software).

TfR 1 Expression In Vitro in Normal and Hypoxic Conditions

TfR 1 expression was determined by western blot analysis with anti-TfR 1 antibody (Ab) (BD Pharmingen) in various cell lines in vitro, including mouse Lewis lung carcinoma (3LL) cells, mouse myoblast (C2C12, a TfR 1-negative cell line as the negative control), human small cell lung cancer cells (NCI-H69, H69-AR, and SW210.5), and human non-small cell lung cancer cells (A549, NCI-H460, NCI-H1975, and PC 9). The expression was also determined when 3LL, A549, PC9, and SW210.5 cells were incubated in 20% oxygen and 1% oxygen (i.e. hypoxic condition).

Multicellular Tumor Spheroids

Multicellular tumor spheroid models consisting of different cancer cell lines were prepared by modifying a previously reported protocol (Friedrich J, et al, *Nature Protocols*, 4:309-324 (2009)). Briefly, 50 µL DMEM medium containing 1.5% agarose (wt/vol) was plated onto each well of a 96-well microtiter plate under sterile conditions. After the agarose solidifies, the plates were stored at room temperature until use. For the penetration study, 5×10$^3$ cells were seeded onto the agarose-plated 96-well plates. After 4-5 days culture to obtain multicellular tumor spheroids (400-500 µm in diameter), the tumor spheroids were carefully transferred into glass bottom dishes. Subsequently, Cy 5-labeled FTn or FTn/FTn-PEG$_x$ (n=2, 5 and 10 kDa) at 40 nM, were added to the dishes. After the 2-hour incubation, the cells were observed using confocal microscopy with Z-stack imaging at ~10 µm intervals. To understand the mechanism by which FTn penetrate spheroid, a competitive binding assay was performed by incubating 3LL cell spheroids with Cy 5-labeled FTn in either the absence or presence of 10-fold molar excess unlabeled FTn for 1 hour. For testing the TfR 1-dependent penetration, the multicellular spheroids were incubated with Cy 5-labeled FTn or FTn/FTn-PEG$_{2k}$ in the absence or presence of 10-fold molar excess Anti-TfR 1 Ab for 1 hour. The 3D images of spheroids were reconstructed by ZEN microscopy software (Carl Zeiss). For analyzing the penetration distance, the radial intensity distribution profile was determined using a custom-made MATLAB code where $\alpha_{tumor}$ is the radius of individual spheroids and r is the radial distance from the spheroid center ($r/\alpha_{tumor}=0$ and 1 indicate the center and edge of the tumor spheroid, respectively). The differences in the radii of tumor spheroids (i.e. $\alpha_{tumor}$) were not statistically significant regardless of varying treatment conditions. Quantification analysis of signal intensity was performed with ImageJ software (NIH).

Results

Western blot analysis probing for TfR 1, a primary receptor for FTn, confirmed TfR 1 expression in human small cell lung cancer (SCLC) cell lines including NCI-H69, H69-AR, and SW210.5 cell lines, and human non-small cell lung cancer (NSCLC) cell lines including A549, NCI-H460, NCI-H1975, and PC9 cell lines. The expression was uniformly elevated in a hypoxic condition (i.e. 1% oxygen) compared to 20% oxygen condition, as shown in 3LL, A549, PC9, and SW210.5 cells.

Confocal microscopic imaging confirmed Cy5-labeled FTn was taken up by mouse Lewis lung carcinoma (3LL) cells efficiently. The uptake of Cy5-labeled FTn by 3LL, as indicated by the intensity of fluorescence signals in cells in flow cytometry analysis, increased as Cy5-labeled FTn increased between 0, 5, 10, 20, 40, and 80 nM (FIG. 3A). FTn-Cy5 uptake was mediated by specific interactions between FTn and TfR 1, as confirmed by the significantly reduced uptake observed in the presence of anti-TfR 1 antibody (Ab) (FIG. 3B). FTn was taken up by another TfR 1-positive human lung cancer cell line, A549, by the same mechanism (FIG. 3B). The uptake of PEGylated FTn with higher PEG MW, including FTn/FTn-PEG$_{2k}$ ($p<0.05$) and FTn/FTn-PEG$_{10k}$ ($p<0.01$), was significantly reduced compared to the uptake of FTn; in contrast, the difference in the uptake of FTn and FTn/FTn-PEG$_{2k}$ was not statistically significant (FIG. 3C). A competitive binding analysis also revealed that FTn and FTn/FTn-PEG$_{2k}$ bound to 3LL cells to a similar extent (FIG. 3D). Additionally, FTn/FTn-PEG$_{2k}$ were efficiently taken up by several TfR 1-positive lung cancer cells, including mouse myoblast (C2C12), human small cell lung cancer cells (NCI-H69, H69-AR, and SW210.5), and human non-small cell lung cancer cells (A549, NCI-H460, NCI-H1975 and PC 9) (FIGS. 3E-3K).

Figure 4F:
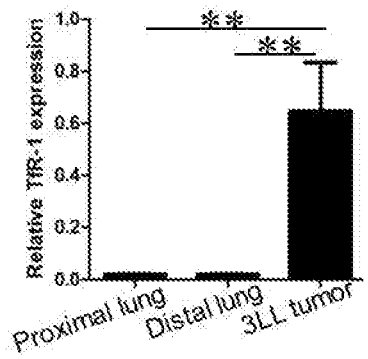

Three-dimensional tumor spheroids formed with 3LL cells were formed to study the effect of PEGylation on the penetration of Cy5-labeled FTn through tumor tissue. The multicellular tumor spheroids constituted the most commonly used in vitro model that recapitulated in vivo tumor microenvironments, as characterized by the presence of naturally formed extracellular matrix (ECM), regions of hypoxia and necrosis (Minchinton A I, et al., *Nature Reviews Cancer*, 6:583-592 (2006)) and concentration gradients of oxygen and nutrients (Lee G Y, et al., *Nature Methods*, 4:359-365 (2007); Abbott A, et al., *Nature*, 424:870-872 (2003)). The 3D-reconstructed confocal images of spheroids revealed that FTn and FTn/FTn-PEG$_{2k}$ uniformly distributed throughout the entire spheroids including the core. In contrast, FTn/FTn-PEG$_{5k}$ and FTn/FTn-PEG$_{10k}$ were primarily near the periphery of tumor spheroids. The mean fluorescence signal intensity was indistinguishable between FTn and FTn/FTn-PEG$_{2k}$, while the FTn/FTn-PEG$_{5k}$ ($p<0.05$) and FTn/FTn-PEG$_{10k}$ ($p<0.01$) exhibited significantly lower intensity compared to FTn (FIG. 4A).

To understand the mechanism of tumor penetration, the penetration of FTn and FTn/FTn-PEG$_{2k}$ was studied. The penetration of Cy5-labeled FTn through the 3D tumor spheroids reduced significantly in the presence of an excess amount of unlabeled FTn ($p<0.01$) (FIG. 4B). The mean fluorescence signal intensities of FTn and FTn/FTn-PEG$_{2k}$ in the 3D-constructed tumor spheroids also significantly decreased in the presence of anti-TfR 1 Ab ($p<0.01$) (FIG. 4C). The TfR 1-dependent tumor penetration was further confirmed with significantly reduced penetration of FTn and FTn/FTn-PEG$_{2k}$ from the surface towards the center, as examined in the middle sections of the tumor spheroids under fluorescence microscopy and quantified in FIG. 4D and FIG. 4E, respectively.

Based on the findings of the aforementioned Examples, the hybrid nanocage formed with 50% ferritin and 50% PEGylated ferritin using PEG$_{2k}$ as the nanoparticle system provided efficient penetration through airway mucus and efficient tumor spheroid penetration in vitro (hereafter, PEG-FTn).

The PEGylated FTn efficiently penetrating tumor tissue in vitro and in vivo, which was in good agreement with previous reports demonstrating widespread dispersion of small PEGylated particles within tumor tissues (Chauhan V P, et al., *Nature Nanotechnology*, 7:383-388 (2012); Nance E, et al., *ACS Nano*, 8:10655-10664 (2014)). However, it was important to select the molecular weight of PEG in addition to its density. As shown in FIG. 4A, non-PEGylated FTn were capable of distributing throughout the entire tumor as effectively as the PEG-FTn, but FTn PEGylated with higher MW PEG were unable to efficiently penetrate tumor tissue. Interestingly as shown in FIGS. 4C-4E, tumor penetration of PEG-FTn was associated with specific interactions between FTn and TfR 1, similar to the mechanism by which PEG-FTn were taken up by cancer cells in FIG. 3B. These results altogether indicated that efficient tumor penetration by PEG-FTn may occur via TfR 1-dependent transcytosis, although the involvement of simple diffusion through the extracellular space within the tumor microenvironment was not fully excluded.

Example 5. PEGylated FTn Penetrated Airway Mucus, Realized Tumor Cell Uptake, and Penetrated Throughout and Located Preferentially within the Tumor Tissue In Vivo Materials and Methods TfR 1 Expression In Vivo In vivo TfR 1 expression was assessed in different tissues, including proximal lung, distal lung, and 3LL subcutaneous tumor. For the preparation of subcutaneous tumor tissues, female C57BL/6 mice (6-8 weeks) were subcutaneously implanted with $1\times10^6$ 3LL cells in the front right flank. The tumor tissues were harvested for assessing TfR 1 expression 10 days after the inoculation.

3LL Cells Constitutively Expressing Reporter Proteins

The following plasmids were used for generating the cells stably expressing reporter proteins. The gene encoding the firefly luciferase Luc 2 was amplified by polymerase chain reaction (PCR) using a forward primer (5'-CGCCATAT-GATGGAAGATGCCAAAAACATTAAG AAGGGCCC-3', SEQ ID:5) and a reverse primer (5'-CGGGATCC-CACGGCGATCTTG CGCCCTT-3', SEQ ID: 6).

The PCR product was subsequently cloned into pLEX plasmid (Thermo Scientific) using NdeI and BamHI as restriction sites. The pReceiver-Lv130 plasmid (GeneCopoeia) was used for achieving the mCherry expression. Lentiviruses packaging Luc 2 or mCherry were prepared using the lentiviral plasmids (Sigma-Aldrich) following the manufacturer's protocol. 3LL cells were incubated with virus (multiplicity of infection~1) for 24 hour, followed by selection with 2 µg/mL puromycin.

Orthotopic Lung Tumor Tissue

For evaluating the distribution of Cy 5-labeled PEG-FTn within the orthotopically established lung cancer, mice (n=6) were inoculated with $1\times10^5$ 3 LL cells stably expressing mCherry (3LL-mCherry; Ex 587 nm, Em 610 nm) via intratracheal intubation. At 10 days post-inoculation, the mice were treated with 50 µL of Cy 5-labeled PEG-FTn (5 µM) using a microsprayer (Model IA-1C-M and FMJ-250 High Pressure Syringe, Penn-Century). The mice were sacrificed 2 hour post-administration, and the entire lungs were isolated and frozen slices were prepared. The co-localization of 3LL-mCherry and PEG-FTn was observed by confocal microscopy.

Results

Figure 4G:
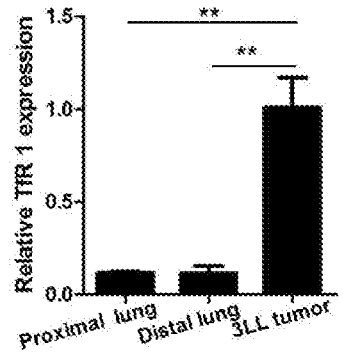

Western blot analysis confirmed the expression of TfR 1 in 3LL-based subcutaneous tumor was over 30-fold higher ($p<0.01$) than that in proximal and distal lung tissues (FIG. 4F) and in 3LL-based orthotopic lung cancer model, TfR-1 was expressed only in the tumor tissue with negligible expression in healthy lung tissues including proximal and distal lungs (FIG. 4G).

An orthotopic mouse model of lung cancer was established by intratracheal inoculation of 3LL cells that constitutively expressed a fluorescent protein, mCherry. Cy5-labeled PEG-FTn was intratracheally administered via a microsprayer 10 days after tumor cell inoculation. Fluorescent microscopy confirmed an orthotopic tumor was established along the airways and infiltrated into the healthy lung parenchyma. Co-localization of intratracheally administered PEG-FTn (i.e. FTn/FTn-PEG$_{2k}$) with an orthotopic 3LL lung cancer (expressing mCherry) was confirmed in confocal microscopy, and PEG-FTn was found preferentially within the tumor tissue.

Figure 5A:
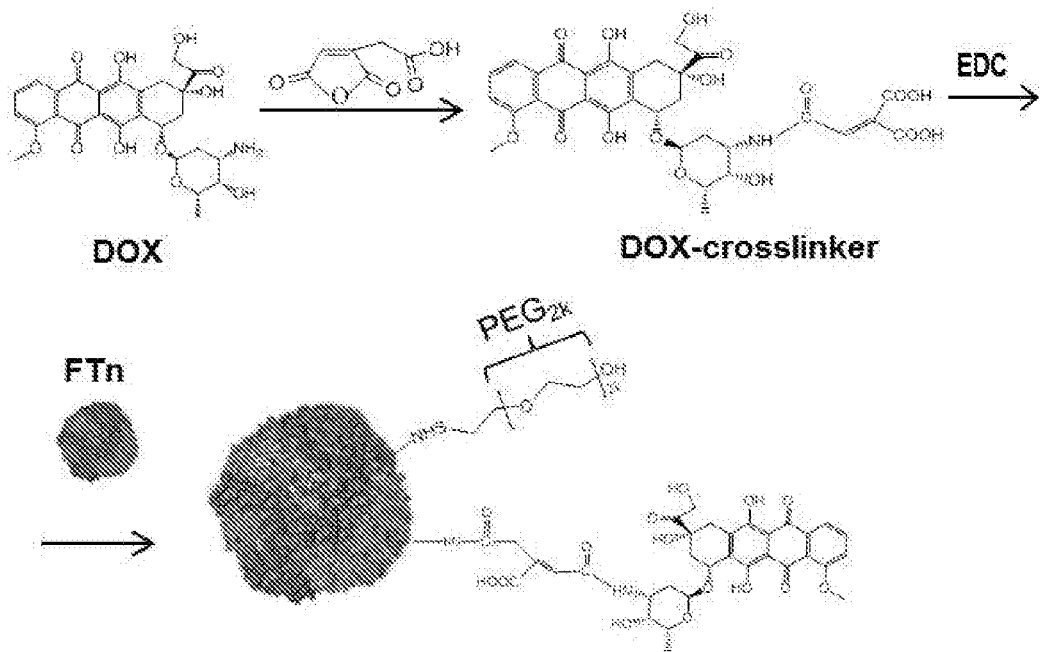

Example 6. Mucosal Delivery of FTn Conjugated with DOX for Release Only after Tumor Cell Uptake and Throughout Tumor Tissue Materials and Methods Conjugation of Doxorubicin (DOX) to Hybrid FTn/PEG-FTn DOX molecules were conjugated to FTn/FTn-PEG$_{2k}$ via acid-sensitive linkers using a modified version of a protocol described previously (Yang H M, et al., Proc Nat Acad Sci USA, 85:1189-1193 (1988)). PEG-FTn denoted the hybrid nanocage formed from 50% FTn and 50% FTn-PEG$_{2k}$. The DOX conjugated PEG-FTn is denoted as FTn/FTn-PEG$_{2k}$/DOX. Briefly as shown in FIG. 5A, 3 mg cis-aconitic anhydride (Sigma) was dissolved in 1 mL p-dioxane (Sigma) aqueous solution (v:v=1:1) and subsequently 2 mg of an ice-cold DOX solution (2 mg/mL in distilled water) was added. The mixture was incubated for 1 hour and 1.5 mg EDC was added to activate a carboxyl group of each DOX-linker conjugate. The resultant compounds were analyzed using high-performance liquid chromatography (HPLC, Varian Inc.) equipped with a C18 reverse phase column. Subsequently, 3 mg the FTn/FTn-PEG$_{2k}$ solution (2 mg/mL, pH 7.4) was reacted with DOX-linker conjugates with activated acid-sensitive linkers for 3 hours. The final product was extensively dialyzed (10 kDa MWCO; Thermo Scientific) and purified with a PD-10 column. The molar ratio of FTn to DOX was determined by measuring protein and DOX concentrations with a Bio-Rad protein assay and measurement of absorbance at 480 nm, respectively. The resulting FTn/FTn-PEG$_{2k}$/DOX was stored at −70° C. until use.

In Vitro Drug Release

To examine pH-sensitive release of DOX, FTn/FTn-PEG$_{2k}$/DOX (200 μM DOX, 500 μL) were placed in a dialysis bag (10 kDa MWCO) and dialyzed against PBS (pH 7.4). At designated times up to 6 days, 150 μL of solution outside the dialysis bag was collected and the same amount of fresh PBS was added back. After 3 days of incubation, the buffer was adjusted to pH 5.0 to induce the release of DOX from PEG-FTn. The concentrations of released free DOX at varying time points were measured by HPLC.

Intracellular Trafficking of FTn Formulations

3LL cells were assayed in the procedures as described in Example 4, but incubated with 10 μM carrier-free DOX or with FTn/FTn-PEG$_{2k}$/DOX (at 10 μM DOX concentration). In order to visualize the intracellular trafficking, 3LL cells were incubated with 40 nM Cy5-labeled FTn/FTn-PEG$_{2k}$ and lysosomes were stained with LysoTracker™.

Multicellular Tumor Spheroids

Multicellular tumor spheroids were prepared and post-treatment analyzed as described in Example 4. Once the tumor spheroids were transferred into glass bottom dishes, DOX (10 μM), FTn/FTn-PEG$_{2k}$/DOX at 10 μM DOX concentration, or no treatment was added to the dish.

In Vitro Cytotoxicity of PEG-FTn-DOX

Cytotoxicity was evaluated by optical imaging of luciferase expression. 3LL cells stably expressing firefly luciferase (3LL-Luc) were treated with various concentrations of PEG-FTn-DOX and DOX for 24 hour. After adding a D-luciferin solution, the bioluminescence imaging was acquired by a Xenogen IVIS Spectrum optical imaging system (Caliper Life Sciences). The luciferase activity was quantified to determine IC$_{50}$ by fitting the data with nonlinear regression using GraphPad Prism.

For cytotoxicity and growth delay experiments of 3D cell spheroids, 5×10$^3$ cells were seeded into the 96-well plates containing agarose. After 3 days, the tumor spheroids were treated with DOX or with FTn/FTn-PEG$_{2k}$/DOX at the final 10 μM DOX concentration and their size was monitored up to 11 days. The diameters of tumor spheroids were recorded with a Zeiss Axiovert 200 phase-contrast microscope (Carl Zeiss) at the indicated time points.

In Vivo Anti-Cancer Efficacy Study

To evaluate the efficacy of PEG-FTn-DOX for treating lung airway cancer, an aggressive orthotopic mouse model was established of proximal lung cancer in inbred mice with intact host immunity. The model was established via intratracheal intubation of cancer cells into the tracheal and bronchial epithelium of lung airways (DuPage M, et al., Nature protocols, 4:1064-1072 (2009)), which was relevant to small cell lung cancer and squamous-cell lung cancer. Briefly, female C57BL/6 mice (6-8 weeks) were inoculated with 2.5×10$^4$ 3 LL-Luc cells in 50 μL of DMEM medium via intratracheal intubation using a 22 G×1" Safelet catheter (Exel International). Three days after the inoculation, bioluminescence signal in the lung was observed using a Xenogen IVIS Spectrum optical imaging system. Subsequently, mice (n=10 per group) were treated with a single dose of DOX (0.25 mg/kg, 50 μL) or FTn/FTn-PEG$_{2k}$/DOX (0.25 mg/kg, 50 μL) administered intratracheally via a microsprayer. The tumor growth was monitored at various time points using an IVIS imaging system and the bioluminescence signal in lung at different time points was quantitatively analyzed by the Living Image® (Caliper Life Sciences) software. The survival of mice was recorded daily, and data was analyzed by Kaplan-Meier survival curve. The mice were monitored three days after cancer cell inoculation and 0, 4, 8, and 11 days after inhaled delivery of DOX or FTn/FTn-PEG$_{2k}$/DOX.

The luciferase activity of 3LL-Luc was visualized and quantified by a Xenogen IVIS Spectrum optical imaging system. In brief, mice were anesthetized with 2% isoflurane in O$_2$ and received intraperitoneal injection of D-luciferin solution in PBS at a dose of 150 mg/kg. Serial images were acquired between 5 and 20 minutes after the D-luciferin administration, and the bioluminescence signal intensity was quantified by the Living Image® software.

Statistical Analysis

Data in all preceding Examples were presented as means±standard error of the mean (SEM). Statistical significance was determined by a two-tailed student's assuming unequal variance. Differences were considered statistically significant at p<0.05. The differences in the survival of mice were analyzed using the log-rank test.

Results

Formulation of DOX-Loaded PEG-FTn

To control the release of DOX to be primarily within tumor cells, the chemotherapeutic drug widely used for airway-related lung cancer therapy was chemically attached to FTn/FTn-PEG$_{2k}$, forming FTn/FTn-PEG$_{2k}$/DOX. Chemically conjugated DOX to FTn/FTn-PEG$_{2k}$ (hereafter, FTn/FTn-PEG$_{2k}$/DOX) via an acid-sensitive linker was designed to achieve high drug loading while enabling drug release only in acidic environments, such as in intracellular endo-lysosomal vesicles (FIG. 5A), as confirmed in HPLC analysis where the retention time of free DOX was about 23 minutes and that of acid activated DOX was about 21 minutes. Transmission electron microscopy confirmed the morphology of FTn/FTn-PEG$_{2k}$/DOX was similar and comparable to that of FTn/FTn-PEG$_{2k}$. Table 2 shows the hydrodynamic diameter and surface charge (as indicated by ζ-potential) of FTn/FTn-PEG$_{2k}$/DOX were comparable to those of FTn/FTn-PEG$_{2k}$. The number of DOX molecules conjugated to each FTn/FTn-PEG$_{2k}$ was 88±5.

TABLE 2

Physicochemical properties of FTn/FTn-PEG$_{2k}$ and FTn/FTn-PEG$_{2k}$/DOX

| | Hydrodynamic diameter (nm) | ζ-potential (mV) | DOX molecules per PEG-FTn |
|---|---|---|---|
| FTn/FTn-PEG$_{2k}$ | 13.6 ± 1.3 | −4.1 ± 1.1 | N/A |
| FTn/FTn-PEG$_{2k}$/DOX | 15.3 ± 3.2 | −7.4 ± 2.8 | 88 ± 22 |

Figure 5B:
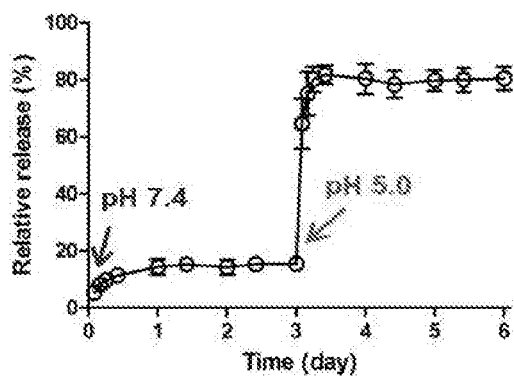

The pH-dependent release kinetics of DOX was evaluated by incubating FTn/FTn-PEG$_{2k}$/DOX in aqueous solutions of varying pH at 37° C. DOX released over 3 days at pH 7.4 was negligible. However, a burst release of DOX was observed upon lowering the pH to 5.0, reaching a maximum release of nearly 80% after 4 hours (FIG. 5B). Confocal images confirmed that FTn/FTn-PEG$_{2k}$ co-localized with lysosomes when incubation with 3LL cells. Free DOX localized only in the cell nucleus 2 hours after its addition to cells, while FTn/FTn-PEG$_{2k}$/DOX was observed in both the cytoplasm and nucleus.

The acid sensitive linker was stable at extracellular neutral or near neutral pH but readily degrade at endolysosomal acidic pH. Although tumor microenvironment can be slightly acidic (pH=6.5-6.8; Wang Y, et al, *Nature Materials*, 13:204-212 (2014)), the specific linker used required substantially lower pH (<6.0) to be degraded (Zhu S, et al, *Adv Mater*, 23:H84-89 (2011)). Results confirmed that DOX molecules were released at pH=5.0 while being stably associated with PEG-FTn at pH=7, and were found both in the cytoplasm and nucleus of lung cancer cells in vitro. In contrast, carrier-free DOX was found only in the nucleus.

Intracellular Fate of DOX-Loaded FTn/FTn-PEG$_{2k}$

To visualize the intracellular trafficking, 3LL cells were incubated with Cy5-labeled FTn/FTn-PEG$_{2k}$ and lysosomes were stained with LysoTracker. Confocal images showed that FTn/FTn-PEG$_{2k}$ colocalized with lysosomes 2 hours after the addition to cells. DOX-loaded FTn/FTn-PEG$_{2k}$ (i.e., FTn/FTn-PEG$_{2k}$/DOX) colocalized with lysosomes labeled with anti-LAMP 1 Ab at the same incubation time. The intracellular fate of DOX administered as free drug compared with FTn/FTn-PEG$_{2k}$/DOX in 3LL cells was analyzed. Free DOX primarily localized in the cell nuclei 2 hours after its addition to cells, whereas FTn/FTn-PEG$_{2k}$/DOX were observed in both the cytoplasm and nucleus. Image-based quantification revealed that, compared with nucleus, ~95% and 55% of DOX delivered via FTn/FTn-PEG$_{2k}$ were found in cytoplasm 30 min and 2 h after adding FTn/FTn-PEG$_{2k}$/DOX to the cells. The findings here collectively suggest that free DOX are taken up by cells by passive diffusion through the cell membrane (Arora H C, et al., *Cancer Res*, 72:769-778 (2012)), whereas FTn/FTn-PEG$_{2k}$/DOX are endocytosed, release DOX in lysosomes, and subsequently the released drug molecules diffuse into cell nuclei.

Penetration of FTn/FTn-PEG$_{2k}$/DOX within Multicellular Tumor Spheroids

FTn/FTn-PEG$_{2k}$/DOX or free DOX at an identical DOX concentration were incubated with 3LL-based tumor spheroids to compare in vitro tumor penetration. 3D-reconstucted confocal images of the spheroids showed that free DOX remained primarily at the periphery of the spheroids, while FTn/FTn-PEG$_{2k}$/DOX uniformly distributed throughout the entire tumor spheroid. Quantification of the DOX signal in the reconstructed 3D images revealed that the mean fluorescence signal intensity of FTn/FTn-PEG$_{2k}$/DOX in the entire spheroid was significantly greater than that of free DOX (p<0.01) (FIG. 6A). Multiple middle section images of the tumor spheroids confirmed that FTn/FTn-PEG$_{2k}$/DOX exhibited a greater 2D-penetration from the surface towards the center compared to free DOX (p<0.01) (FIG. 6B). Improved penetration of FTn/FTn-PEG$_{2k}$/DOX compared to free DOX was also observed in other tumor spheroid models constructed with human lung cancer cell lines, including A549, H460, and H1975 (FIGS. 6C, 6D, and 6E).

The in vitro tumor-killing capacity of FTn/FTn-PEG$_{2k}$/DOX was compared with that of free DOX using 3LL cells constitutively expressing luciferase. The IC$_{50}$ of DOX and FTn/FTn-PEG$_{2k}$/DOX were 0.48 and 1.1 µM, respectively (FIG. 6F). Despite the higher IC$_{50}$, FTn/FTn-PEG$_{2k}$/DOX provided superior ability of delaying the growth of 3LL tumor spheroids compared to free DOX (p<0.05) (FIG. 6G), likely due to increased penetration.

Figure 7A:
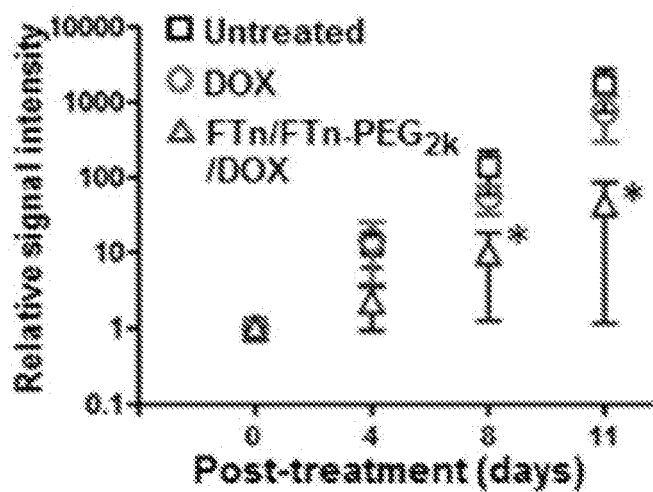
Figure 7B:
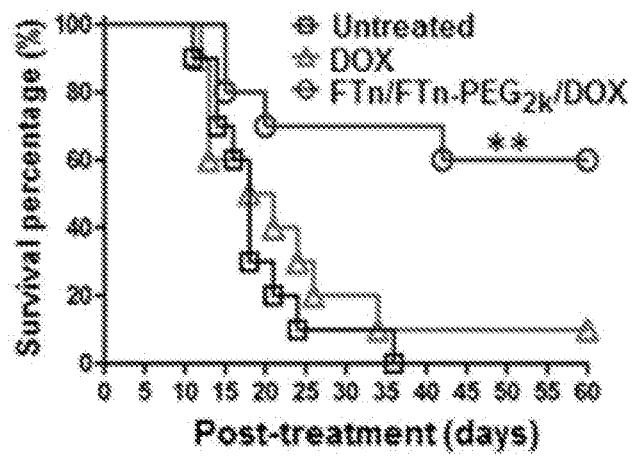

In Vivo Efficacy of FTn/FTn-PEG$_{2k}$/DOX Against an Orthotopic Mouse Lung Cancer Model A proximal lung cancer model was established by intratracheally inoculating 3LL cells that constitutively expressed luciferase (Day −3). Three days after the inoculation, tumor cells were detected by bioluminescence imaging throughout the upper airways (Day 0). Subsequently, tumor growth was monitored over time. A single intratracheal dosing of free DOX or FTn/FTn-PEG$_{2k}$/DOX was administered at Day 0. Bioluminescence imaging at Days 0, 4, 8, and 11 showed mice treated with FTn/FTn-PEG$_{2k}$/DOX exhibited a significant delay in tumor progression compared to mice that were either untreated or treated with free DOX (n=10 mice per group). FTn/FTn-PEG$_{2k}$/DOX effectively inhibited tumor growth, as reflected by a 40-fold and 17-fold decrease in signal intensity (from luciferase-expressing tumor cells) (p<0.05) compared to mice that were untreated and mice that were treated with free DOX, respectively, 11 days after treatment (FIG. 7A). Survival was also significantly improved for mice treated with FTn/FTn-PEG$_{2k}$/DOX compared to untreated and free DOX-treated mice (p<0.01). In this orthotopic mouse model of highly aggressive airway lung cancer, treatment with FTn/FTn-PEG$_{2k}$/DOX resulted in a 60% progression-free survival after 60 days, compared to a median survival of only 18 days in animals treated with an equivalent dose of free DOX and in untreated animals (FIG. 7B).

Example 7. Intravenous Injection of Densely PEGylated FTn Targeted Subcutaneous Tumor and Lung Cancer Materials and Methods Tumor uptake of PEGylated FTn following systemic administration was studied based on the findings in Example 2 that densely PEGylated FTn provided an excellent colloidal stability in physiological conditions, efficient tumor cell uptake, and tumor tissue penetration. Specifically, densely PEGylated FTn formulated with 75% PEGylated ferritin protein with PEG MW of 2, 5 and 10 kDa and labeled with a fluorescent tag were intravenously injected into mice bearing subcutaneous 3LL tumor (i.e., flank tumor). Eighteen hours after the administration, the tumor tissues were extracted from mice and imaged to quantify for the epi-fluorescence radiance in different treatment groups.

An orthotopic mouse model of aggressive lung cancer was also established based on 3LL cells. Implantation of tumor cells into the organ of origin ("orthotopically") allowed organotypical interaction between tumor cells and surrounding stroma. The expressions of TfR 1 in proximal lung, distal lung, and 3LL tumor were analyzed via western blot analysis with TfR 1 Ab. Densely PEGylated FTn formulated with PEGylated ferritin protein was systemically administered via intravenous injection. The distribution of the densely PEGylated FTn was analyzed via histochemical analysis of the orthotopic tumor tissue and surrounding lung tissue at 3 hours post-injection.

Results

Figure 8:
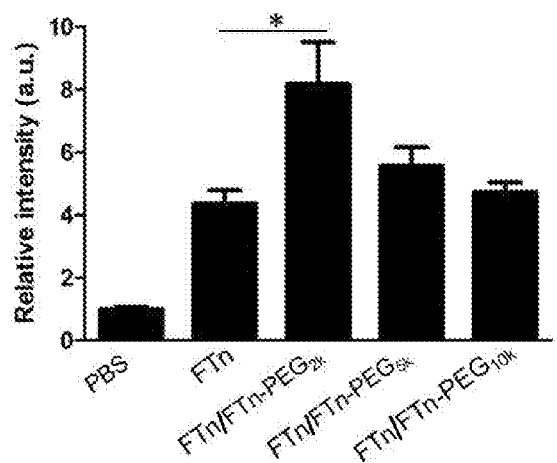
FIG. 8 is a bar graph showing the relative bioluminescence signal of subcutaneous (flank) tumors in mice eighteen hours after intravenously administered phosphate buffered saline (PBS), non-PEGylated FTn, or PEGylated FTn formulated with 75% PEGylated ferritin protein with PEG MW of 2, 5, or 10 kDa.

FIG. 8 shows densely PEGylated FTn formulated with 2k Da PEG provided a significantly greater tumor partition from systemic circulation, compared to non-PEGylated FTn and FTn PEGylated with higher MW PEG. Densely PEGylated FTn, formulated with 75% ferritin protein PEGylated with 2 kDa PEG, partitioned into, and distributed throughout, the tumor tissue, including hypoxic tumor regions, as confirmed by fluorescent microscopy of tumor and surrounding tissues.

In the 3LL orthotopic lung cancer model at 3 h post-injection, preferential distribution of PEGylated FTn in the tumor over healthy tissue was apparent, as confirmed by fluorescent microscopy of tumor and surrounding tissues.

The circulating, densely PEGylated FTn partitioned into and distributed throughout the tumor tissue, including hypoxic tumor regions. The signal intensity in hypoxic regions increased over time (0.5 h, 3 h, 8 h, 18 h) following intravenous injection. After 18 h injection, the signal in hypoxic regions were significantly higher than normoxic regions.

Figure 9:
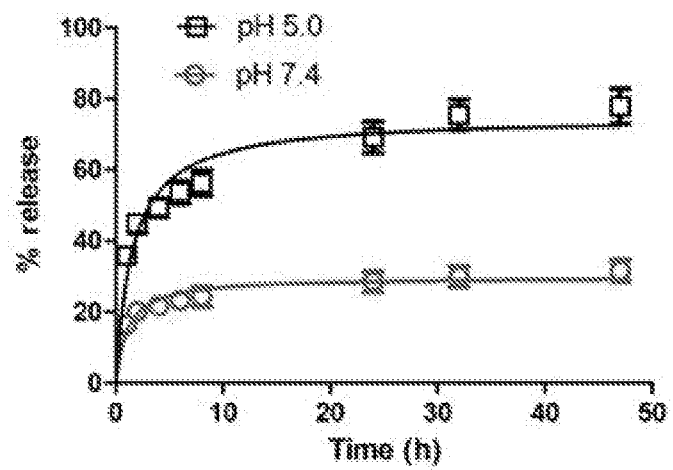
FIG. 9 is a line graph showing the percentage of release (%) of acriflavine from acriflavine-loaded pegylated FTn (denoted FTn/FTn-PEG$_{2k}$/AF) re-assembled from 75% pegylated FTn and 25% non-pegylated FTn over time (hour) in a pH 5.0 medium compared to the release in a pH 7.4 medium.

Example 8: Encapsulation of a Therapeutic Agent into PEGylated FTn Via a Nanocage Re-Assembly Process with Decreasing Concentrations of Urea Acriflavine (AF), an inhibitor of hypoxia-inducible factor 1 (HIF-1) dimerization, was loaded into the inner cavity of 75% PEGylated FTn in a serial concentration of urea solutions (8M, 7M, 5M, 3M, 2M, 1M, and 0M). The ferritin protein dissociated in 8M urea, and slowly reassembled along a decreasing concentration of urea. With acriflavine in the solution, the re-assembly process of FTn encapsulated acriflavine in the process. TEM images showed cage-like structure of FTn/FTn-PEG$_{2k}$/AF (containing ~60 AF per nanocages). Drug release kinetics confirmed AF release was pH-dependent (FIG. 9).

Following incubation with 3LL cells, western blotting analysis confirmed both AF and FTn/FTn-PEG$_{2k}$/AF inhibited Hif-1α expression. The inhibition was dose-dependent, i.e., increasing the amount of AF in the free AF or that in FTn/FTn-PEG$_{2k}$/AF from 0.625 µM to 1.25 µM, further to 2.5 µM, decreased the level of Hif-1α expression. The inhibition was also time-dependent, i.e., the inhibition was more prominent after a 6 hour-incubation than a 24 h-incubation, and even more prominent than a 48 h-incubation. Hif-1α, a marker for tumor hypoxia, is an indicator of cancer progression, metastasis, and drug resistance in clinic.

Figure 10:
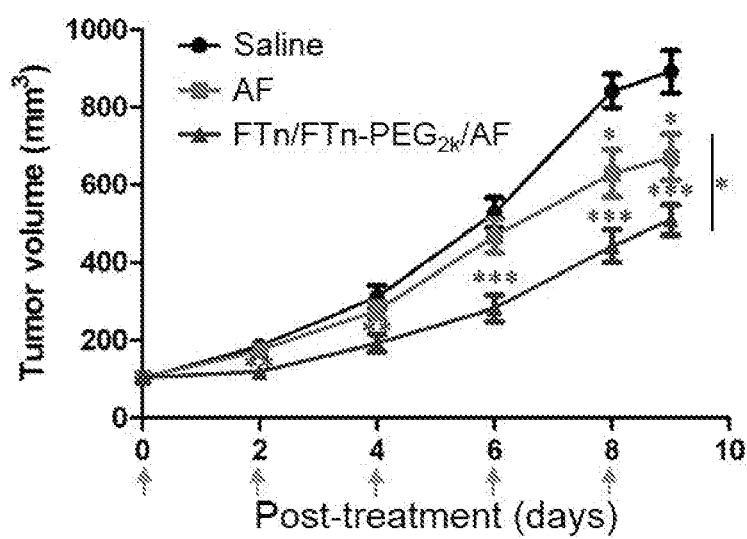
FIG. 10 is a line graph showing the tumor volume (mm$^3$) over post-treatment time (days) of animals containing a 3LL subcutaneous tumor model. The animals were administered at day 0, 2, 4, 6, and 8 via tail vein injection with (1) FTn/FTn-PEG$_{2k}$/AF, (2) AF, or (3) saline.

FTn/FTn-PEG$_{2k}$/AF was injected at the tail vein to assay the effect on tumor growth in a 3LL subcutaneous tumor model at several time points (0, 2, 4, 6, and 8 days post tumor development). At day 10 post tumor development, the tumor volume was reduced in the animals treated with AF, as well as in the animals treated with FTn/FTn-PEG$_{2k}$/AF treatment. The inhibition by FTn/FTn-PEG$_{2k}$/AF was significantly more prominent than that induced by administering free AF alone (FIG. 10).

We claim:

1. A protein nanocage comprising: self-assembling proteins or peptides assembled to form a protein nanocage, a surface altering agent comprising linear and/or branched polyalkylene oxide or copolymers thereof adsorbed to the surface of the protein nanocage or covalently bound to at least some of the self-assembling proteins or peptides,
wherein the surface altering agent is covalently bound to at least 25% of the self-assembling proteins or peptides, wherein the surface altering agent is coated onto the protein nanocage in a number density between about 0.1 and about 0.5 polyalkylene oxide/nm2 of the surface area of the protein nanocage, or wherein the polyalkylene oxide is covalently bound to the self-assembling proteins or peptides at a density of between 4 and 20 polyalkylene oxide per self-assembling protein or peptide, and a therapeutic, prophylactic, or diagnostic agent adsorbed, covalently bound to, or encapsulated in the protein nanocage.

2. The protein nanocage of claim 1, wherein the surface altering agent is covalently bound to at least 25% of the self-assembling proteins or peptides.

3. The protein nanocage of claim 2 wherein the protein nanocage comprises 24 ferritin heavy chains or a variant thereof having at least 90% homology to the ferritin heavy chain, which self-assemble into a protein nanocage at a neutral or near neutral pH.

4. The protein nanocage of claim 1, wherein the surface altering agent is polyethylene glycol or a block copolymer thereof having a molecular weight between 300 Da and 100,000 Da.

5. The protein nanocage of claim 4, wherein the molecular weight of the polyethylene glycol or block copolymer thereof is between about 300 Da and about 5 kDa.

6. The protein nanocage of claim 1, wherein the surface altering agent is coated onto the protein nanocage in a number density between about 0.1 and about 0.5 polyalkylene oxide/nm$^2$ of the surface area of the protein nanocage.

7. The protein nanocage of claim 1, wherein the polyalkylene oxide is covalently bound to the self-assembling proteins or peptides at a density of between 4 and 20 polyalkylene oxide per self-assembling protein or peptide.

8. The protein nanocage of claim 1, wherein the therapeutic, prophylactic, or diagnostic agent is covalently bound to the protein nanocage via a degradable linker.

9. The protein nanocage of claim 8, wherein the degradable linker is an acid-labile compound containing a hydrazone or a cis-aconityl group.

10. The protein nanocage of claim 8, wherein the therapeutic agent comprises an anti-proliferative agent, anti-angiogenesis agent, analgesic agent, anti-inflammatory drug, antipyretics, antiepileptics, antipsychotic agent, neuroprotective agent, anti-infectious agent, antihistamines, antimigraine drug, antimuscarinics, anxiolytic, sedative, hypnotics, antipsychotics, bronchodilators, anti-asthma drug, cardiovascular drug, corticosteroid, dopaminergic, gastro-intestinal drug, muscle relaxant, parasympathomimetic, stimulant, anorectics, immune checkpoint inhibitor, or anti-narcoleptics.

11. The protein nanocage of claim 10 wherein the therapeutic agent is a chemotherapeutic, anti-angiogenic agent, immune checkpoint inhibitor, or anti-proliferative agent.

12. The protein nanocage of claim 11 wherein the therapeutic agent is selected from the group consisting of alkylating agents, antimetabolites, anthracyclines, plant alkaloids, topoisomerase inhibitors, monoclonal antibodies or fragment thereof, and tyrosine kinase inhibitors.

13. The protein nanocage of claim 10 wherein the agent is selected from the group consisting of doxorubicin, dexrazoxane, sorafenib, erlotinib hydrochloride, cisplatin, cetuximab, sunitinib, bevacizumab carboplatin, oxaliplatin, mechlorethamine, cyclophosphamide, chlorambucil, vincristine, vinblastine, vinorelbine, vindesine, taxol, irinotecan, topotecan, amsacrine, etoposide, etoposide phosphate, teniposide, epipodophyllotoxins, trastuzumab, rituximab, acriflavine, digitoxin, digoxin, rapamycin, thalidomide, topotecan, pembrolizumab, nivolumab, atezolizumab, avelumab, durvalumab, and combinations thereof.

14. The protein nanocage of claim 1 in a formulation comprising a pharmaceutically acceptable excipient.

15. A method of making the protein nanocage of claim 1 comprising:
    combining a plurality of self-assembling proteins or peptides or assembled nanocages in a solution, wherein at least 25% of the self-assembling peptides or proteins comprises surface altering agents;
    adjusting the pH to strong acidity or basicity or increasing the concentration of urea in the solution;
    and incubating the solution at a neutral or near neutral pH or removing urea from the solution to form protein nanocages.

16. The method of claim 15 wherein the solution further comprises a therapeutic, prophylactic or diagnostic agent, and the agent is encapsulated during the formation of the protein nanocages.

17. A method of administering one or more therapeutic, prophylactic, or diagnostic agents to an individual in need of lung cancer treatment, the method comprising administering an effective amount of the protein nanocage of claim 1.

18. The method of claim 17, wherein the protein nanocage is administered to a mucosal tissue using a method of administration selected from the group consisting of intranasal administration, vaginal administration, administration to the gastrointestinal tract, administration to the eye or a compartment thereof, pulmonary administration, rectal or colonic administration, sublingual administration, buccal administration, oral administration, and topical administration to an ocular area.

19. The method of claim 17, wherein the protein nanocage is administered by injection.

* * * * *